United States Patent
Patel et al.

(10) Patent No.: US 8,206,420 B2
(45) Date of Patent: Jun. 26, 2012

(54) SPINOUS PROCESS DEVICE AND METHOD OF USE

(75) Inventors: Nirali Patel, Murietta, CA (US); Thomas Purcell, Del Mar, CA (US)

(73) Assignee: Alphatec Spine, Inc, Carlsbad, CA (US)

( * ) Notice: Subject to any disclaimer, the term of this patent is extended or adjusted under 35 U.S.C. 154(b) by 223 days.

(21) Appl. No.: 12/462,858

(22) Filed: Aug. 10, 2009

(65) Prior Publication Data

US 2010/0036419 A1 Feb. 11, 2010

Related U.S. Application Data

(60) Provisional application No. 61/188,417, filed on Aug. 8, 2008, provisional application No. 61/194,983, filed on Oct. 1, 2008, provisional application No. 61/167,067, filed on Apr. 6, 2009.

(51) Int. Cl.
*A61B 17/70* (2006.01)
(52) U.S. Cl. .................. 606/249; 606/247; 606/248
(58) Field of Classification Search ........... 606/246–253
See application file for complete search history.

(56) References Cited

U.S. PATENT DOCUMENTS

| | | | | |
|---|---|---|---|---|
| 6,652,527 | B2 * | 11/2003 | Zucherman et al. | 606/249 |
| 7,048,736 | B2 * | 5/2006 | Robinson et al. | 606/86 B |
| 7,621,939 | B2 * | 11/2009 | Zucherman et al. | 606/249 |
| 7,635,378 | B2 * | 12/2009 | Zucherman et al. | 606/249 |
| 7,658,752 | B2 * | 2/2010 | Labrom et al. | 606/249 |
| 7,727,233 | B2 * | 6/2010 | Blackwell et al. | 606/71 |
| 7,871,426 | B2 * | 1/2011 | Chin et al. | 606/248 |
| 2003/0040746 | A1 * | 2/2003 | Mitchell et al. | 606/61 |
| 2003/0187435 | A1 * | 10/2003 | Lin | 606/61 |
| 2003/0216736 | A1 * | 11/2003 | Robinson et al. | 606/61 |
| 2006/0036240 | A1 | 2/2006 | Colleran et al. | |
| 2008/0183218 | A1 * | 7/2008 | Mueller et al. | 606/280 |
| 2010/0087860 | A1 * | 4/2010 | Chin et al. | 606/249 |

FOREIGN PATENT DOCUMENTS

| | | |
|---|---|---|
| GB | 780652 | 8/1957 |
| WO | WO03007829 | 1/2003 |

* cited by examiner

*Primary Examiner* — Eduardo C Robert
*Assistant Examiner* — Stuart S Bray
(74) *Attorney, Agent, or Firm* — Michael R. Shevlin

(57) ABSTRACT

A spinous process device and method are disclosed. The device includes a first plate having a first part slidably coupled to a second part, a second plate having a third part slidably coupled to a fourth part, and first and second connector devices configured to be placed through openings created in spinous processes and rotatably couple respective first and second parts to third and fourth parts of the first and second plates together allowing angular displacement of the second plate with respect to the first plate and secure the spinous processes between the first and second plates.

15 Claims, 32 Drawing Sheets

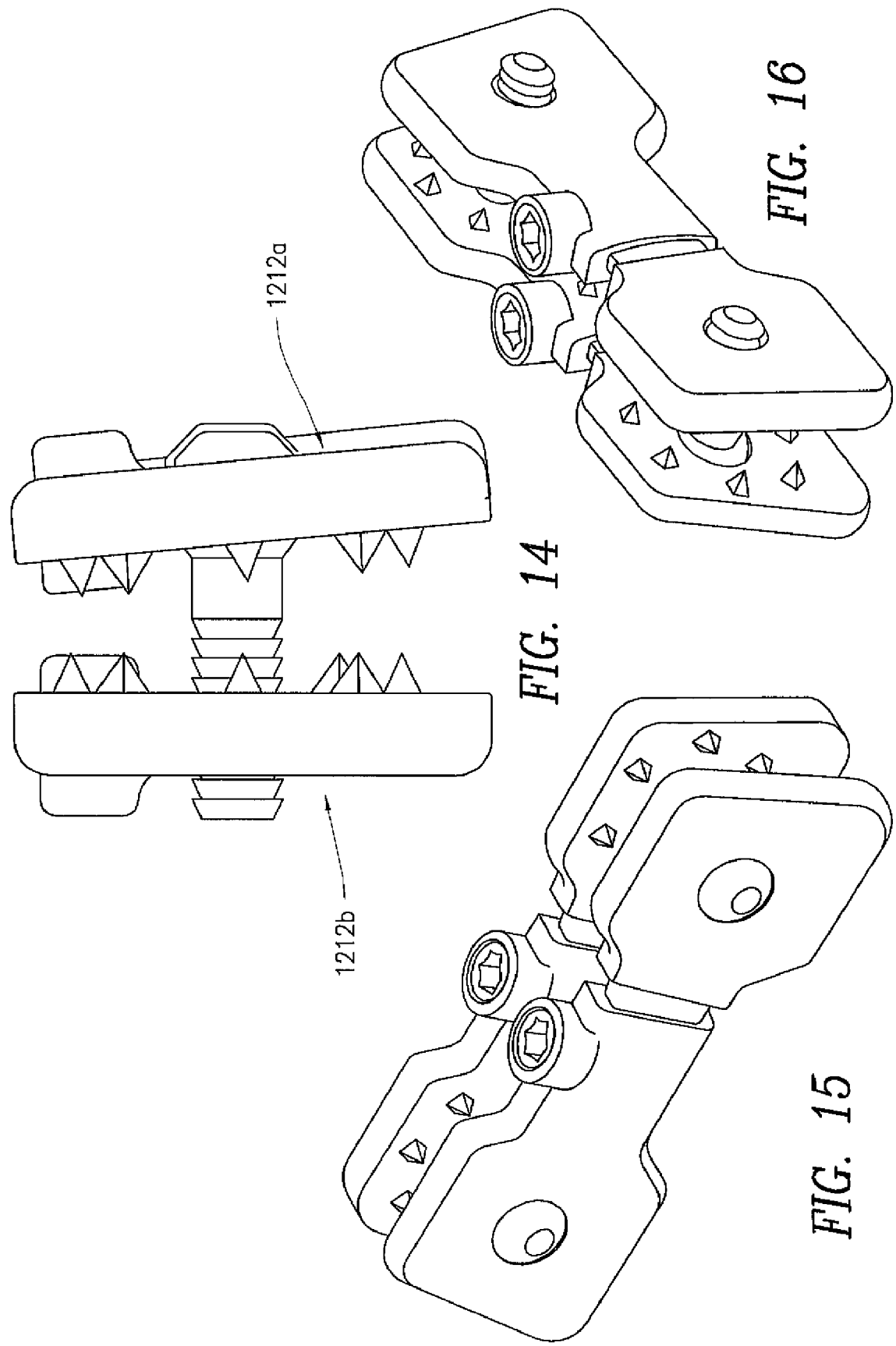

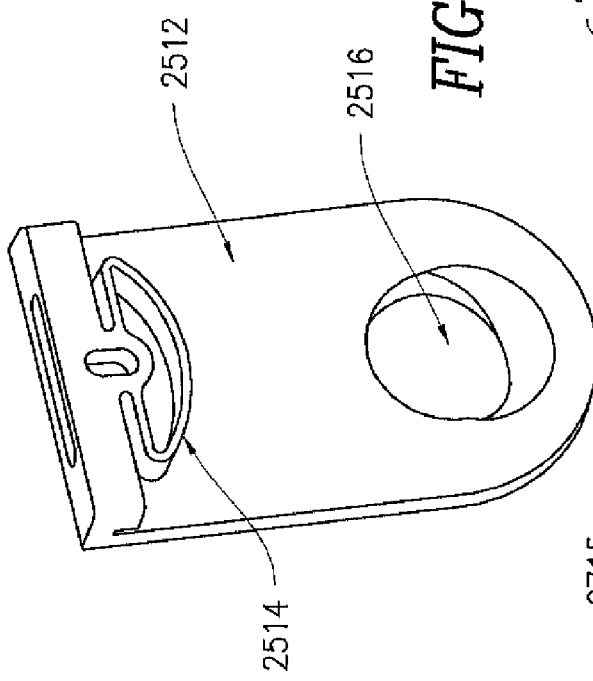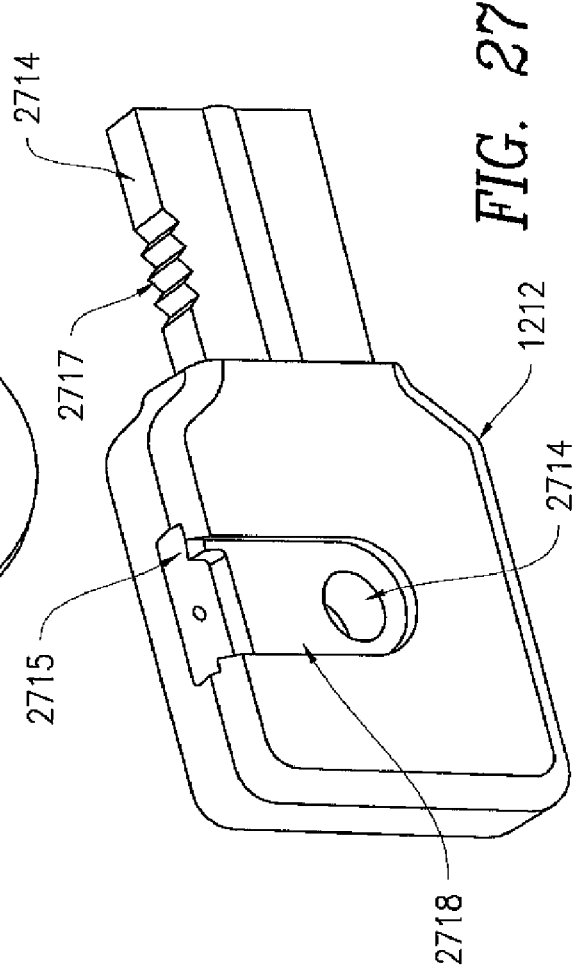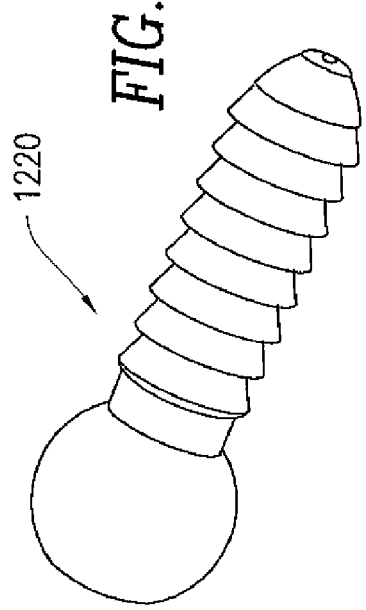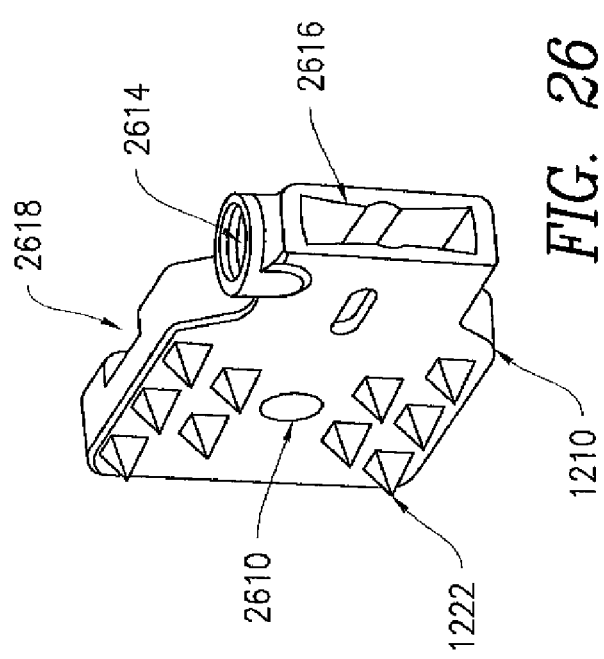

SPINOUS PROCESS DEVICE AND METHOD OF USE

CROSS-REFERENCE TO RELATED APPLICATIONS

The present application claims priority to U.S. Provisional Patent Application Nos. 61/188,417, filed Aug. 8, 2008, 61/194,983, filed Oct. 1, 2008, both entitled "Spinous Process Device", and 61/167,067, filed Apr. 6, 2009, entitled "Spinous Process Device And Method Of Use", the disclosures of which are incorporated herein by reference in their entirety.

BACKGROUND OF THE INVENTION

1. Field of the Invention

Embodiments of the present invention generally relate to the field of surgery, and more specifically, to a clamping device for securing various parts of a spinous process.

2. Background of the Invention

The spinous process of a vertebra is directed backward and downward from the junction of the laminae (in humans), and serves for the attachment of muscles and ligaments. A typical vertebra consists of two essential parts: an anterior (front) segment, which is the vertebral body; and a posterior part—the vertebral (neural) arch—which encloses the vertebral foramen. The vertebral arch is formed by a pair of pedicles and a pair of laminae, and supports seven processes, four articular, two transverse, and one spinous, the latter also being known as the neural spine.

When the vertebrae are articulated with each other, the bodies form a strong pillar for the support of the head and trunk, and the vertebral foramina constitute a canal for the protection of the medulla spinalis (spinal cord). In between every pair of vertebrae are two apertures, the intervertebral foramina, one on either side, for the transmission of the spinal nerves and vessels.

Two transverse processes and one spinous process are posterior to (behind) the vertebral body. The spinous process comes out the back, one transverse process comes out the left, and one on the right. The spinous processes of the cervical and lumbar regions can be felt through the skin. Superior and inferior articular facets on each vertebra act to restrict the range of movement possible. These facets are joined by a thin portion of the neural arch called the pars interarticularis.

Further features and advantages of the invention, as well as structure and operation of various embodiments of the invention, are disclosed in detail below with references to the accompanying drawings.

SUMMARY OF THE INVENTION

In some embodiments, the present invention relates to a spinous process device including a first plate having a first part slidably coupled to a second part, a second plate having a first part slidably coupled to a second part, and first and second connector devices configured to be placed through openings created in spinous processes and rotatably couple respective first and second parts to third and fourth parts of the first and second plates together allowing angular displacement of the second plate with respect to the first plate and secure the spinous processes between the first and second plates.

In many embodiments, the device further includes first and second locking mechanisms configured to lock the first and second parts and the third and fourth parts a desired distance apart.

In many embodiments, each plate includes an interior portion having a plurality of protrusions configured to interact with the bony matter.

In many embodiments, upon connection of the first and second plates using the first and second connector devices, the first and second plates are configured to be parallel to each other.

In many embodiments, upon connection of the first and second plates using the first and second connector devices, the first and second plates are configured to be disposed at an angle with respect to each other.

In many embodiments, the connector devices are selected from a group consisting of: screws, bolts, pins, springs, rods, and other suitable devices.

In many embodiments, each of the first and second parts includes an opening configured to accommodate the first and second connector device.

In many embodiments, at least one of the first part and the second part includes an angularly disposed flange configured to form an angle with at least one of the first part and the second part.

In some embodiments, the present invention relates to a spinous process device including a first portion translationally coupled to a second portion, first and second bone attachment mechanisms coupled to the first and second portions and configured to secure the first and second portions to first and second spinous processes, a translational mechanism configured to allow the first and second portions to translate with respect to each other, varying the distance between the first and second bone attachment mechanisms, and a locking mechanism configured to lock the first and second portions at the desired distance between the first and second bone attachment mechanisms.

In many embodiments, the first bone attachment mechanism includes a first rod configured to be inserted into an opening created in the first spinous process and a clamping washer configured to couple with the first rod and secure the first portion to the first spinous process, the second bone attachment mechanism includes a second rod configured to be inserted into an opening created in the second spinous process and a clamping washer configured to couple with the second rod and secure the second portion to the second spinous process.

In many embodiments, the device further includes a plurality of protrusions disposed on the first and second portions configured to interact with the first and second spinous processes.

In some embodiments, the present invention relates to a spinous process device including a fixation plate having a plurality of slotted openings, a plurality of fixation devices adjustably coupled to the slotted openings and configured to be placed through openings created in a first and second spinous processes, and clamping washers configured to couple with the fixation devices and secure the fixation plate to the spinous processes in the desired compression or distraction position.

In many embodiments, the fixation devices are selected from a group consisting of: screws, bolts, pins, springs, rods, and other suitable devices.

In some embodiments, the present invention relates to a spinous process device including a first plate configured to be pivotally coupled to a second plate, a clamping mechanism configured to couple the first plate to the second plate upon pivotal movement of the plates toward each other, and a plurality of protrusions disposed on at least one of the plates and configured to interact with spinous processes to be secured by the plates, wherein the spinous processes are positioned between the plates.

In some embodiments, the present invention relates to a spinous process device including a first plate having a first part rotatably and translationally coupled to second part along a first pivot axis, a first arm extending transversely from the first part relative to the first pivot axis configured to extend between a first and second spinous processes, a second plate having a third part rotatably and translationally coupled to a fourth part along a second pivot axis, a second arm extending transversely from the third part relative to the second pivot axis configured to extend between the first and second spinous processes, and a coupling mechanism configured to engage the first and second arms and angularly and translationally couple the first and second plates.

In many embodiments, the first arm includes a rod and the coupling mechanism includes a clevis having a body with an aperture, the body being coupled to the second arm and the aperture being coupled to the rod, wherein the distance between the first plate and the second plate is adjustable by sliding the rod relative to the second arm while the rod extends through the aperture of the clevis, and wherein the first part and the third part are rotatable relative to each other by rotating the second arm about the rod within aperture of the clevis.

In many embodiments, the coupling mechanism includes a body having a first coupler opening, a second coupler opening, a third coupler opening and a base opposite the first coupler opening, the second and third coupler openings being on opposite sides of the body and configured to receive the first and second arm and a securing screw coupled to the first couple opening configured to clamp the first and second arms between the securing screw and the base.

In many embodiments, the first part includes a first extended portion receivable into a hollow interior portion of the second part and the third part includes a second extended portion receivable into a hollow interior portion of the fourth part, the device further including a first securing screw coupling the first part to the second part and a second securing screw coupling the third part to the fourth part.

In many embodiments, at least one of the first part, second part, third part and fourth part includes an interior surface with a plurality of protrusions configured to interact with the spinous process.

In some embodiments, the present invention relates to a spinous process device including a first plate extending along a first pivot axis including a first part configured to abut a first spinous process and a second part configured to abut a second spinous process, wherein the first part is slidably coupled to the second part along the first pivot axis and the second part is rotatable relative to the first part, a second plate extending along a second pivot axis including a third part configured to abut the first spinous process opposite the first part and a fourth part configured to abut the second spinous process opposite the second part, wherein the third part is slidably coupled to the fourth part along the second pivot axis and the fourth part is rotatable relative to the third part, and a coupling mechanism configured to couple the first and second plates such that the distance between the first plate and the second plate is adjustable and the first part and the third part are rotatable relative to each other.

In many embodiments, the first part includes a first member extending toward the third part, and the third part includes a second member extending toward the first part, wherein the first member is coupled to the second member with the coupling mechanism that allows the first member to translate axially and rotate relative to the second member to establish a spaced distance between the first part and the third part and to establish an angular relationship between the first part and the third part.

In many embodiments, the coupling mechanism includes a clevis, the clevis comprising an aperture, a body and a threaded end, wherein the first member is a rod and the second member is an arm, the rod being coupled to the arm with the rod extending through the aperture and translating axially through the aperture to establish a spaced distance between the first part and the third part, and the arm rotates about the clevis body to establish an angular relationship between the first part and the third part.

In many embodiments, the coupling mechanism includes a hollow cylinder having a first opening, a second opening, and a third opening, the first member is a first arm and the second member is a second arm comprising a threaded hole, wherein the first plate is coupled to the second plate with the first arm received in the second opening of the hollow cylinder, the second arm received in the third opening of the hollow cylinder, and wherein a securing screw extends into the first opening of the hollow cylinder and engages the threaded hole in the second arm.

In many embodiments, at least one of the first part, second part, third part and fourth part includes an interior surface with a plurality of protrusions configured to interact with the spinous processes.

In some embodiments, the present invention relates to a method of clamping adjacent spinous processes including providing a spinous process device including a first plate having a first part slidably coupled to a second part, a second plate configured to be placed oppositely to the first plate and having a third part slidably coupled to a fourth part, first and second connector devices configured to be placed through openings created in the spinous processes and couple first and second parts of the first plate to second and third parts of the second plate together, creating openings in the spinous processes at a predetermined distance apart to receive the first and second connector devices, adjusting the distance between the first and second parts of the first plate and the second and third parts of the second plate so that the first and second connector devices are aligned with the openings in the spinous processes, the spinous processes being disposed between the plates, and securing the first and second plates to the spinous processes with the first and second connector devices, thereby compressing and clamping the spinous processes between the first and second plates.

In some embodiments, the present invention relates to a method of clamping adjacent spinous processes including providing a spinous process clamping device including a first part and a second part slidingly coupled to form a first plate, a third part and a fourth part slidingly coupled to form a second plate, a coupling mechanism configured to couple the first and second plates to allow for adjustment of distance and relative rotation between the first and second plates, inserting the spinous process clamping device adjacent at least two adjacent spinous process with the first plate provided on one side of the two adjacent spinous processes and the second plate provided on the other side of the two adjacent spinous process, clamping the first plate and second plates to the opposite sides of the two adjacent spinous processes, wherein said clamping includes adjusting lengths of the first plate and the second plate by sliding the first part relative to the second part and sliding the third part relative to the fourth part, respectively, to a desired length for placement of the first and second plates against the two adjacent spinous processes, adjusting an angular relationship of the first and second parts of the first plate by twisting the first part relative to the second part, and adjusting the angular relationship of the third and fourth parts of the second plate by twisting the third part relative to the fourth part, to conform to the shape of the adjacent spinous processes, and adjusting an angular relationship of the first plate relative to the second plate via the coupling mechanism connecting the first plate to the second plate, to conform to the shape of the adjacent spinous processes.

BRIEF DESCRIPTION OF THE DRAWINGS

Embodiments of the present invention are described with reference to the accompanying drawings. In the drawings, like reference numbers indicate identical or functionally similar elements. Additionally, the left-most digit(s) of a reference number identifies the drawing in which the reference number first appears.

FIGS. 12-27 are various views of another exemplary embodiment of the spinous process clamp, according to some embodiments of the present invention.

DETAILED DESCRIPTION OF THE INVENTION

As required, detailed embodiments of the present invention are disclosed herein; however, it is to be understood that the disclosed embodiments are merely examples of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Embodiments of the present invention relate to a spinal process clamp. The clamp can be used during surgical techniques such as preservation or removal of the posterior spinous ligament, unilateral vs. bilateral dissection, bony preparation techniques, grafting technique, and other techniques. The clamp can be used medially or laterally. The clamp can be coupled through spinous process, between spinous process, superior/inferior to the spinous process, posterior to the spinous process, or anywhere else. The coupling mechanism can include a threaded nut and bolt through the dorsal plane, a ratchet, a threaded interference screw in the axial plane (direct A/P).

The clamp can be also translated using various translation and locking mechanisms. The translation mechanism includes slotted holes, sliding washers, interlocking plates, coupled rods, or any other devices. The locking mechanism includes a ratchet, interference screws, teeth with compression screw, or any other locking mechanisms.

Figure 1:
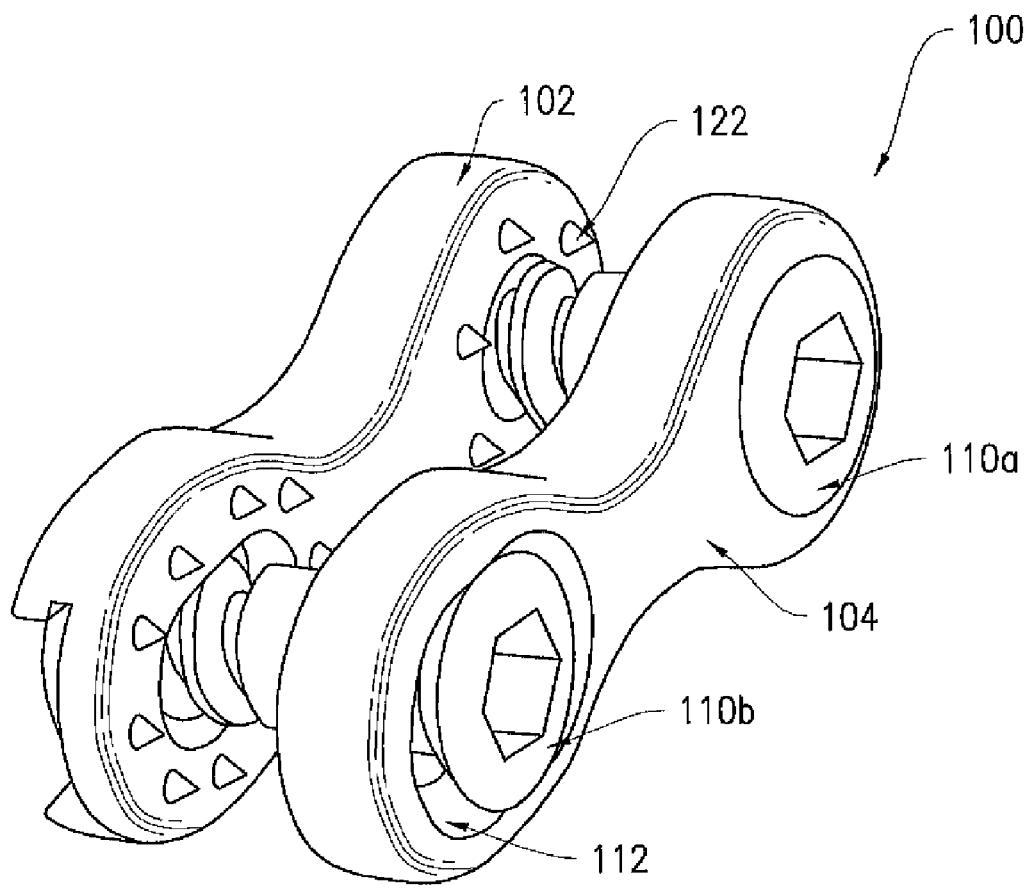
FIG. 1 is a perspective view of an exemplary spinous process clamp, according to some embodiments of the present invention.
Figure 2:
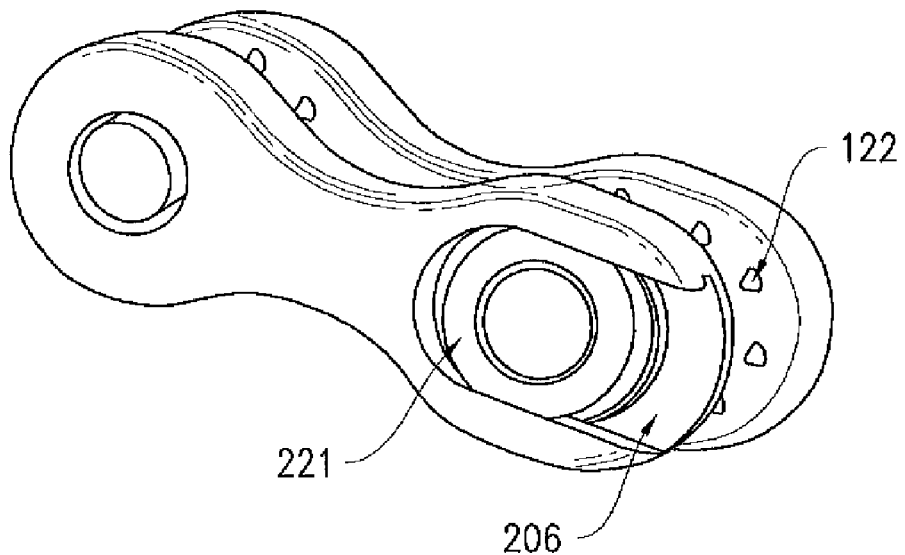
FIG. 2 is another perspective view of the spinous process clamp shown in FIG. 1.

FIGS. 1-2 illustrate an exemplary embodiment of a spinous process clamp 100, according to some embodiments of the present invention. The clamp 100 uses threaded screws to couple and compress the plates to the spinous process. The clamp 100 is stable and is easy to manufacture.

The clamp 100 includes a first curved plate 102 and a second curved plate 104 coupled together via threaded screws 110 (a, b). The curved plates 102, 104 include two end portions configured to accommodate placement of screws 110 and a middle portion disposed between the end portions. In some embodiments, the end portions of the plates 104 are configured to be enlarged so as to accommodate openings for the placement of threaded screws 110. In some embodiments, one of the openings can be enlarged (see, numeral 112) so as to accommodate sliding/translation of the screws 110 and thus, adjustable securing of the screw 110. Such adjustable securing allows for adjusting the distance between the screws 110 during installation of the clamp 100. To allow for the adjustable securing of the threaded screw 110b, the plate 102 can include a sliding nut 221 that can be securing within a recess 206 disposed on the plate 102. The sliding nut 221 includes a threading that accommodate threads of the threaded screw 110b. Screw 110a can be configured to be threadedly secured within a corresponding threaded opening of the plate 102.

Figure 28A:
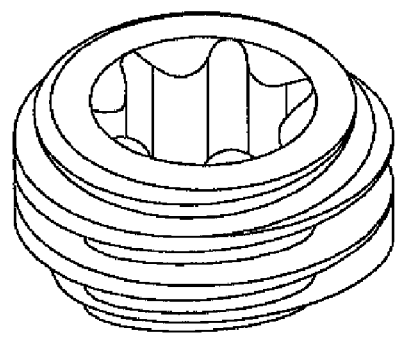
FIGS. 28a-28c are various views of an exemplary hexa-globe screw that can be used in connection with the present invention's spinous process clamps, according to some embodiments of the present invention.
Figure 28B:
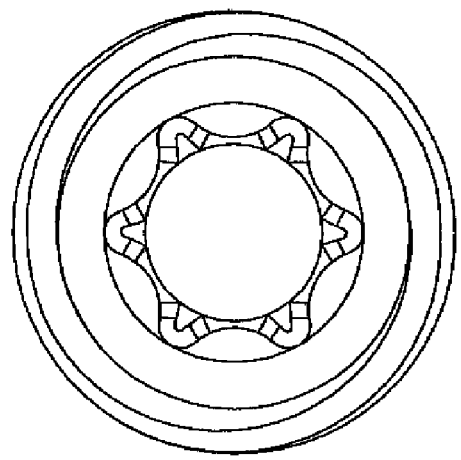
Figure 28C:
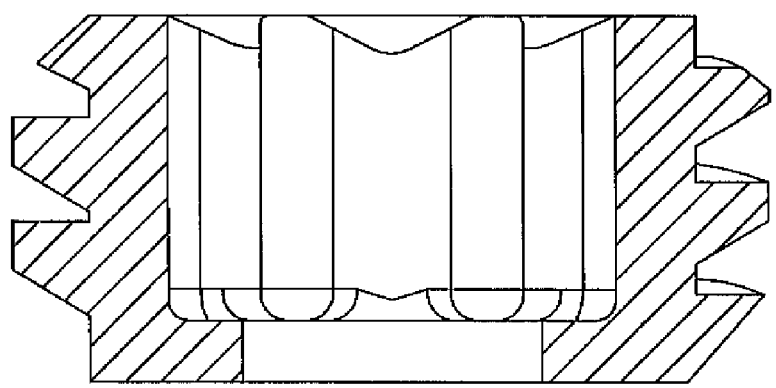

In some embodiments, to further secure plates 102, 104, each plate can include protrusions 122 that are disposed on the interior facets of the plates 102, 104, as shown in FIG. 1. Such protrusions 122 can be configured to extend toward each other when the plates 102, 104 are coupled together using screws 110. The protrusions 122 are configured to create additional friction between the bony matter and the plates. The protrusions 122 can be sharp and have a conical, pyramidal, or any other desired shape. The distance between the plates 102, 104 can be adjusted upon securing the plates 102, 104. This process is referred to as compression. The screws 110 are configured to include recesses configured to accommodate use of special type wrenches for rotating the screws. The recesses can be hexagonal (as shown in FIG. 1), hexaglobal (which, in some embodiments, can be a combination of hexagonal and star-like shape, as shown in FIGS. 28a-c), or any other type of recesses. In some embodiments, in order to secure the clamp 100 to the bone, two holes corresponding in diameter to the diameter of the screws are created in the bony matter. The plates are attached at opposite sides of the bones and the screws are protruded through the openings in the plates and the created holes. Then, the screws are threadedly secured to the plates.

The clamp 100 is useful in scenarios where installation of parallel plates 102, 104 conforms to the human anatomy and the recess 206 of the plate 102 does not interfere with adjacent levels after compression. In some embodiments, the lateral locking screws may be difficult to tighten and holes made in spinous process may weaken the bone.

Figure 3:
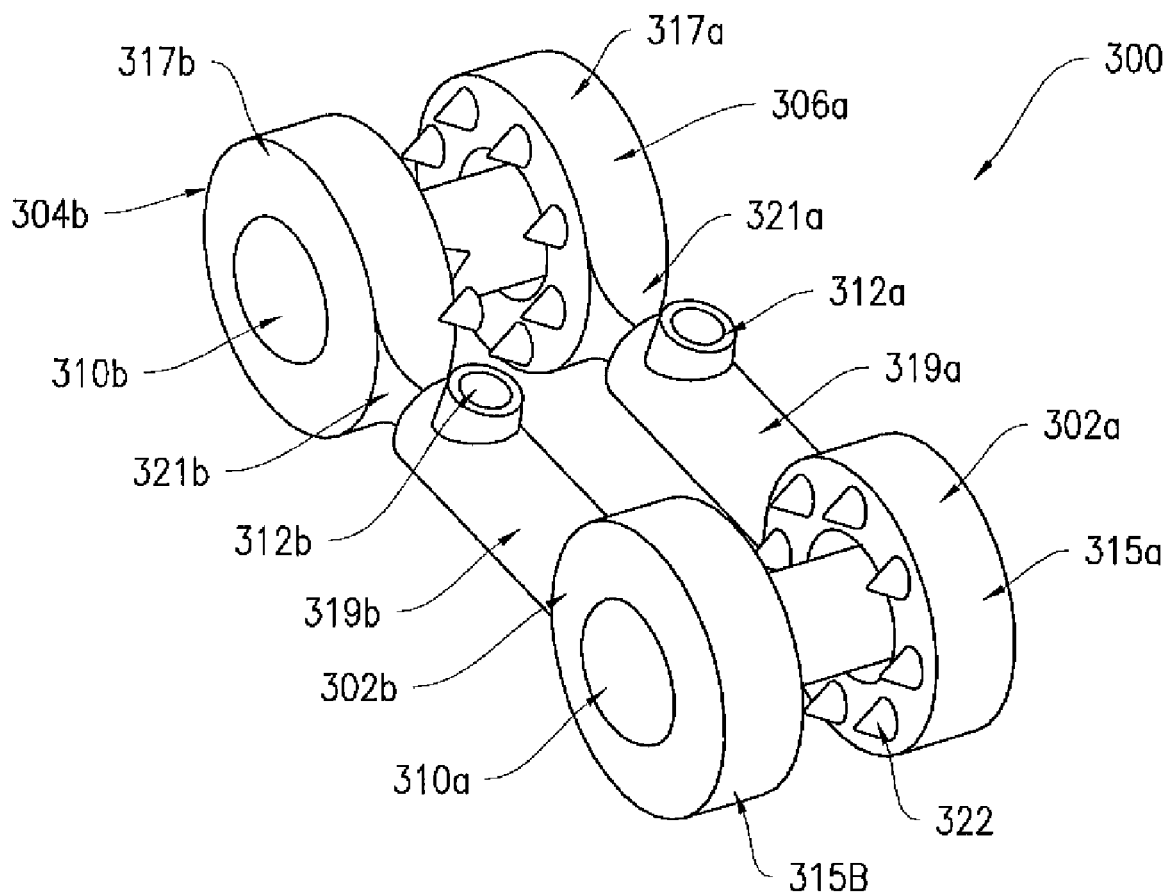
FIG. 3 is a perspective view of another exemplary spinous process clamp, according to some embodiments of the present invention.
Figure 4:
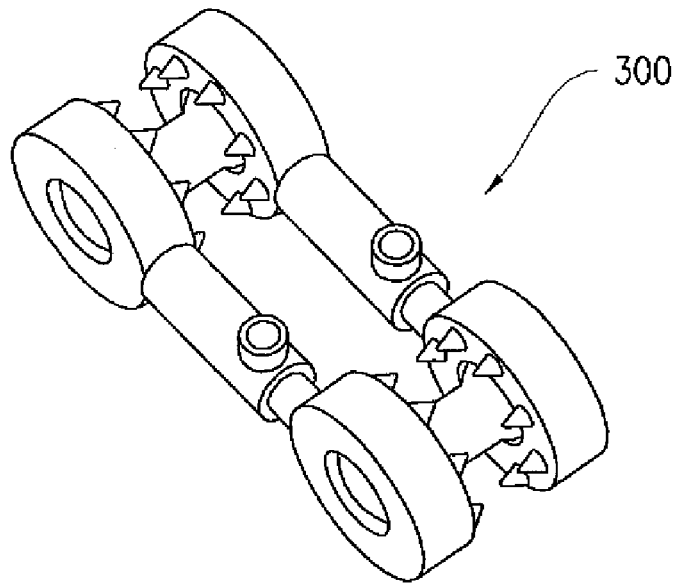
FIG. 4 is another perspective view of the spinous process clamp shown in FIG. 3.

FIGS. 3-4 illustrate another exemplary spinous process clamp 300, according to some embodiments of the present invention. Clamp 300 is configured as a ball-and-socket design and conforms to the anatomy of the patient. The clamp 300 includes stationary portions 302 (a, b) and mobile portions 304 (a, b). The stationary portions 302 include screw securing portions 315 (a, b) coupled to respective holder portions 319 (a, b). The mobile portions 304 also include screw securing portions 317 (a, b) coupled to respective sliding rod portions 321 (a, b). The holder portions 317 are configured to have a hollow interior and further configured to be larger in diameter than the rod portions 321, wherein the rod portions 321 are configured to slide inside the hollow interiors of the respective holder portions 317. The holder portions 319 further include clamping screws 312 (a, b), respectively, that are configured to secure the rod portions 321 once they are inserted into the hollow holder portions 319. Such sliding arrangement between stationary portions 302 and mobile portions 304 allows adjustment of length between respective screw securing portions 315 and 317, hence, the device 300 can be configured to span a greater distance between sections of a bony matter. The screw securing portions 315 and 317 are configured in a similar fashion as the screw securing portions shown in FIGS. 1-2. Also, similar to the device 100 shown in FIGS. 1-2, the screw securing portions 315 and 317 include protrusions 322 disposed on inner surfaces of the portions 315 and 317 and configured to face each other when the device 300 is assembled. The protrusions 322 are configured to be coupled to the bony matter and prevent slippage of the device 300. The portions 319 and 321 can be configured to have a parallelepiped, cylindrical, or any other desired shape. The screw securing portions 315, 317 can have a round, oval, square, rectangular, or any other desired shape.

The following are some of the advantages of the device 300 shown in FIGS. 3-4. The ball-and-socket design of the device 300 allows fixation surfaces to conform to the anatomy of the bony matter. Additionally, dynamic struts (portions 319, 321) allow for compression and distraction without interference with the adjacent structures. Also, direct posterior interference screw (screws 312) facilitates simple locking of the translation. The device 300's non-incremental translation allows for infinite adjustability.

Figure 5:
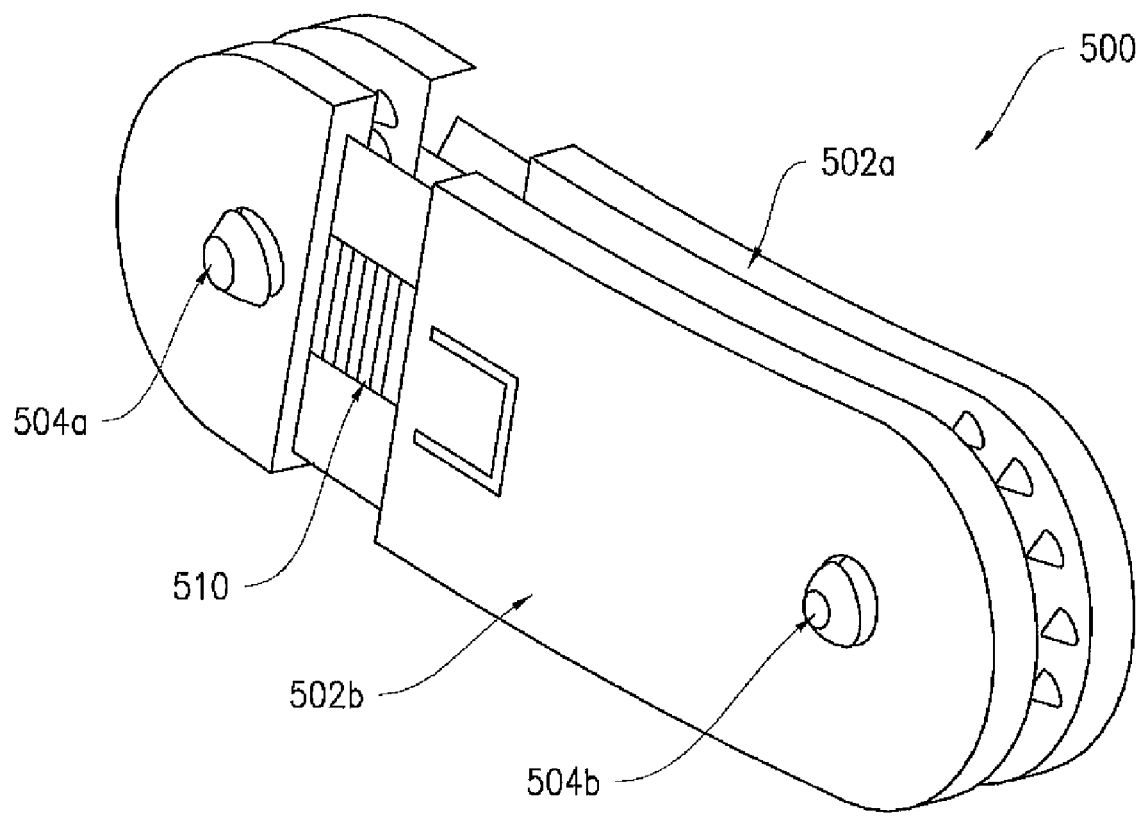
FIG. 5 is a perspective view of yet another exemplary spinous process clamp, according to some embodiments of the present invention.
Figure 6:
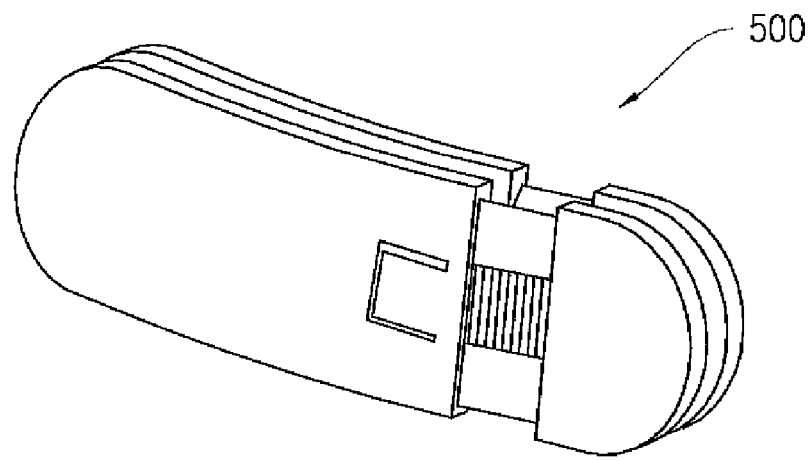
FIG. 6 is another perspective view of the spinous process clamp shown in FIG. 5.

FIGS. 5-6 illustrate another exemplary spinous process clamp/device 500, according to some embodiments of the present invention. The clamp 500 has a narrow profile, does not include additional locking steps and does not interfere with adjacent anatomy. The device 500 uses mating "dovetail" plates having ratchets in order to achieve controlled compression and distraction. Apposing plates of the device 500 are coupled with a ratcheting snap ring and boss that automatically locks when compressed.

As shown in FIGS. 5-6, the device 500 includes plates 502(a, b) that are configured to appose each other when the device 500 is assembled. The plates 502 are coupled together using screws (or other connection devices) 504 (a, b). In some embodiments, the plates 502 are configured to be parallel to each other when coupled together using screws 504. In some embodiments, the plates 502 can be disposed at an angle with regard to each other when coupled together. The screws 504 are configured to couple plates 502 at opposite ends of the plates 502. Each one of the plates 502 includes a ratcheting mechanism 510 that is configured to adjust distance between the screws 504. The ratcheting mechanism 510 includes a plurality of ratchets that allow step-wise increase in distance between the screws 504.

Figure 7:
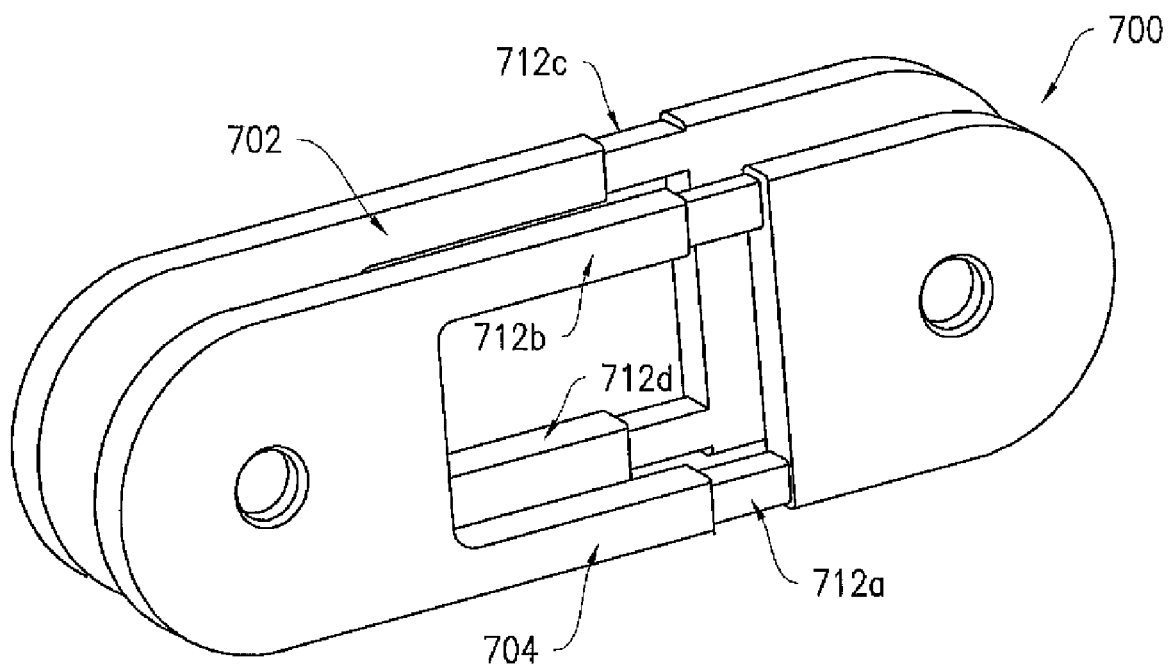
FIG. 7 is a perspective view of yet another exemplary spinous process clamp, according to some embodiments of the present invention.
Figure 8:
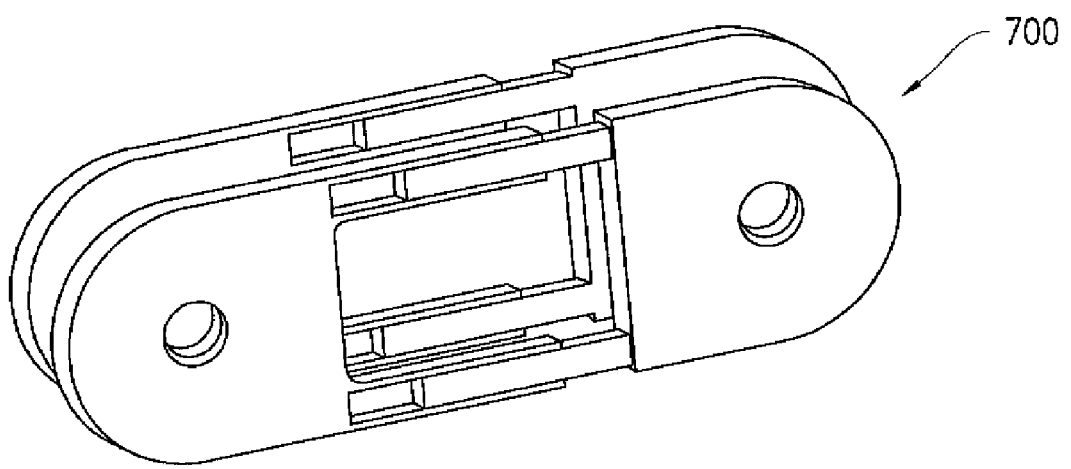
FIG. 8 is another perspective view of the spinous process clamp shown in FIG. 7.

FIGS. 7-8 illustrate another exemplary spinous process clamp 700, according to some embodiments of the present invention. The clamp 700 includes sliding plates 702 and 704 that are configured to appose each other and coupled to each other using screws or any other connection means. The clamp 700 is configured to be coupled with an interspinous device in order to help support a segment. The clamp 700 includes similar translation and fixation mechanism discussed with regard to FIGS. 1-6 above. Each sliding plate 702, 704 includes sliding ramps 712 (a, b, c, d) that are disposed in the mid-section of the plates and allows a back-and-forth translation of the plates. The clamp 700 is configured to provide additional support to an interspinous graft and does not interfere with adjacent levels.

Figure 9:
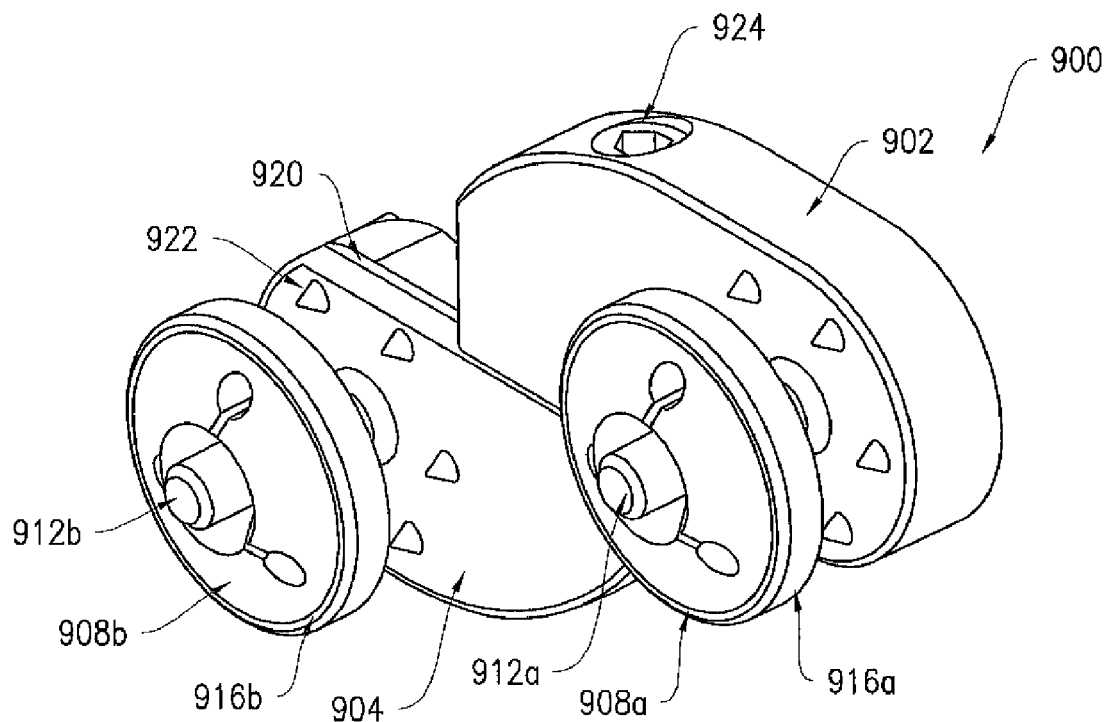
FIG. 9 is a perspective view of another exemplary spinous process clamp, according to some embodiments of the present invention.

FIG. 9 illustrates yet another exemplary spinous process device 900, according to some embodiments of the present invention. The device 900 is a segmental spinous process plate which allows for compression or distraction. Stair-step/off-set design allows for easier use on multiple segments. Fixation of device 900 can be done through a hole in the spinous process. In some embodiments, the device 900 can be used for placement of two plates with connection through the interspinous ligament. The device 900 can be placed laterally, thereby preserving spinous process ligaments. It further allows for an infinite adjustment during compression or distraction fixation. In some embodiments, the device 900 can be secured through holes within spinous process and allows a multi-level use.

The device 900 includes a first portion 902 and a second portion 904. The portions 902 and 904 are configured to be slidingly coupled to each via a translational mechanism 920. The translational mechanism 920 is configured to allow portions 902, 904 to translate with respect to each other, thus, varying the distance between bone attachment mechanisms 908 (a, b). Upon achieving a desired distance between bone attachment mechanisms 908, the portions 902, 904 are configured to be secured to each other using a clamping screw 924. To release the portions 902, 904 from one another, the screw 924 is released. The bone attachment mechanisms 908 include rods 912 (a, b) configured to be coupled to the portions 902, 904, respectively. The mechanisms 908 (a, b) further include clamping washers 916 (a, b). The washers 916 (a, b) are configured to be securely fastened to the respective rods 912 (a, b) and thus, secure the device 900 to the bony matter in a desired location. Similarly to the devices described above, the portions 902, 904 and/or the washers 916 (a, b) can include a plurality of protrusions 922 that are configured to prevent slippage of the device 900 along the bony matter. As stated above, the use of the translational mechanism 920 allows fixation of the device 900 to the boney matter at any place, thereby spanning the desired distance between bone segments.

Figure 10:
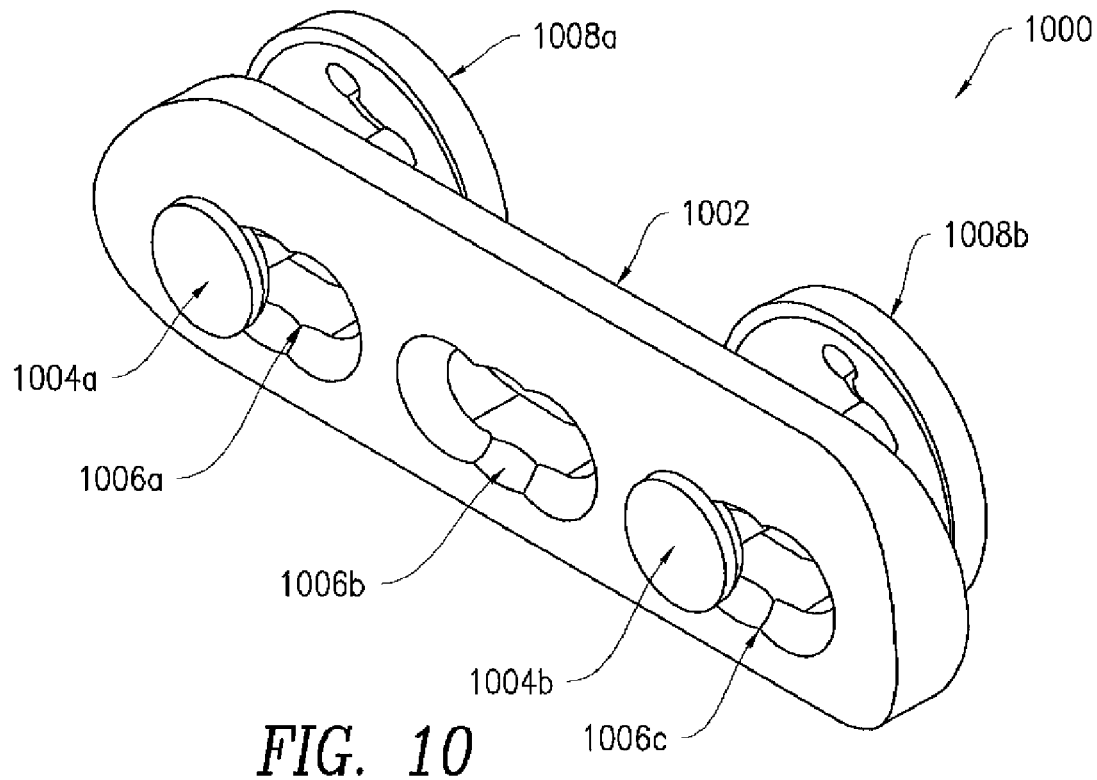
FIG. 10 is a perspective view of yet another exemplary spinous process clamp, according to some embodiments of the present invention.

FIG. 10 illustrates yet another exemplary spinous process fixation device 1000, according to some embodiments of the present invention. The device 1000 includes a main plate 1002 having a plurality of openings 1006 (a, b, c). Each of the openings 1006 is configured to be contoured to accommodate placement of fixation devices/screws/bolts 1004 (a, b), as shown in FIG. 10. As can be understood by one skilled in the art, the fixation or connector devices can be screws, bolts, pins, springs, rods, or any other connector devices. To install the device 1000 to the spinous process, a surgeon (or any other medical professional) creates two openings in the bony matter, places the main plate 1002 inserts fixation devices 1004 (a, b) through the openings 1006 (a, b, c) and the created openings in the bony matter and secures them with clamping washers 1008 (a, b) (similar to those shown in FIG. 9). The device 1000 provides for a simple slotted plate that can be attached through the spinous process. The device 1000 can be configured to allow for several other options including: 1) using two plates with attachment through spinous process; 2) attaching a spiked device into slots and attaching two plates through the interspinous ligament. The device 1000 can be placed laterally, thereby preserving spinous process ligaments. In some embodiments, it also allows to incrementally adjust for compression or distraction fixation. Similarly to the devices described above, the plate 1002 and/or the washers 1008 can include a plurality of protrusions that are configured to prevent slippage of the device 1000 along the bony matter.

Figure 11:
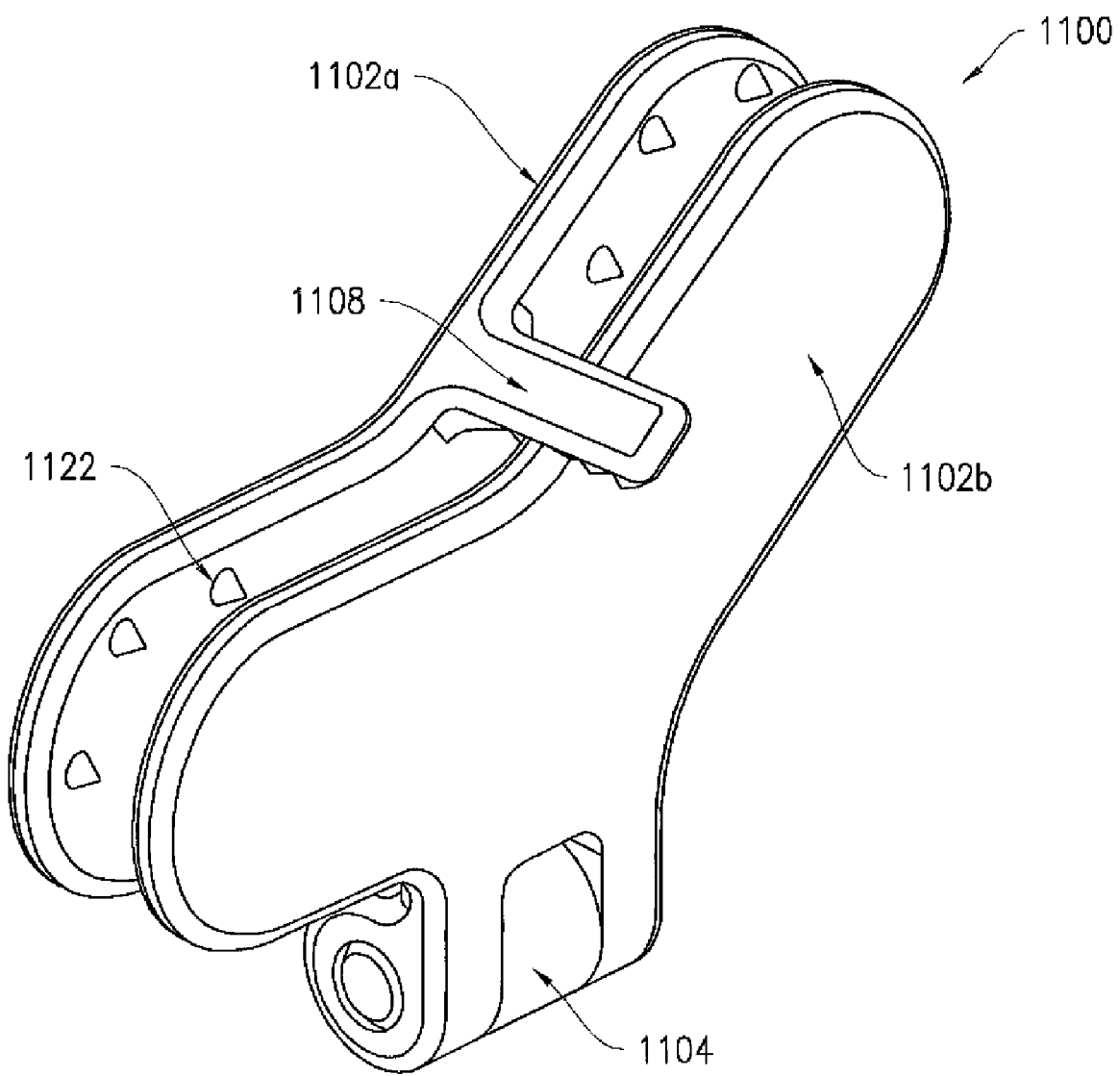
FIG. 11 is a perspective view of yet another exemplary spinous process clamp, according to some embodiments of the present invention.

FIG. 11 illustrates yet another exemplary spinous process device 1100, according to some embodiments of the present invention. The device 1100 includes two hingedly coupled plates 1102 (a, b). In some embodiments, the plates 1102 have a butterfly shape and are coupled using a hinge 1104 that is disposed near a narrower segment of the plates 1102 so as not to interfere with the attachment to the bony matter. To install the device 1100, the device is placed around the bone and then the plates are pivoted to close the "butterfly wings" of the plates 1102 around the bone. In some embodiments, the interior portions of the plates 1102 include protrusions 1122 (similar to the protrusions of the above devices shown in FIGS. 1-10) that are configured to prevent slippage of the plates 1102. The plates 1102 further include a clasping mechanism 1104 that upon closing holds the plates together.

The device 1100 allows posterior implant approach between spinous processes through a smaller incision. In some embodiments, the device 1100 can be secured to spinous processes without creating holes through spinous process. It also allows a multi-level use. In some embodiments, interspinous process placement does not interfere with posterior instrumentation (i.e. pedicel screws).

Figure 12:
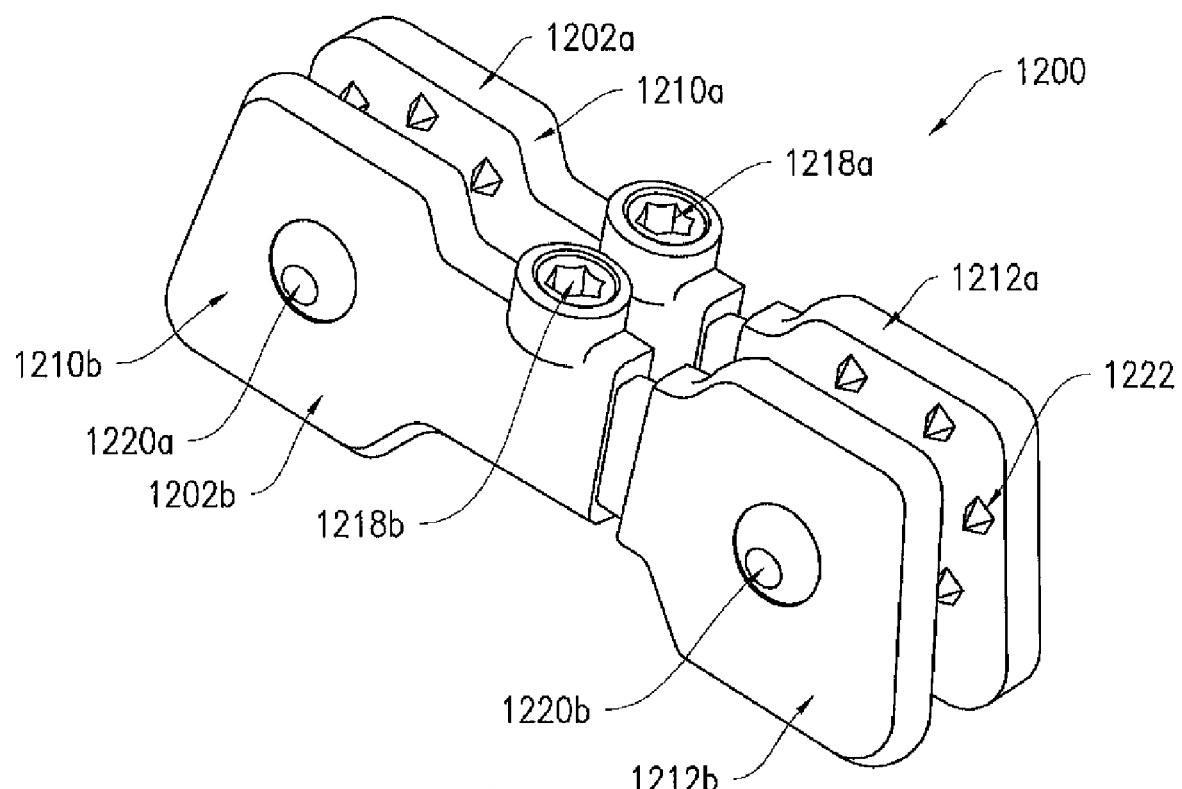

FIGS. 12-27 illustrate another exemplary spinous process device 1200, according to some embodiments of the present invention. The device 1200 is configured to incorporate some of the features of the devices described above with regard to FIGS. 1-11. The device 1200 includes a first plate 1202a and a second plate 1202b that are angularly coupled to each other via connecting screws/bolts/devices 1220a, 1220b. Each plate 1202 is configured to include sliding parts 1210 and 1212. The parts 1210 (a, b) and 1212 (a, b) are configured to be translationally coupled in the mid-section of the plates 1202 (a, b), thereby allow adjustment of distance between the connecting devices 1220. To secure a particular distance between the connecting devices 1220 (a, b), each of the plates 1202 (a, b) includes a securing screw 1218. This arrangement is similar to the one shown in FIGS. 3-4. In some embodiments, a portion of the part 1210 (a, b) is configured to fit inside an interior of at least a portion of the part 1212 (a, b) and allow for a translational movement of the parts 1210 and 1212 with respect to each other, as shown in FIG. 12. Upon translating the parts to a desired distance, a rotational force is applied to the screw 1218 to secure such distance. Each of the plates 1202 include interior and exterior portions. The interior portions are configured to be placed adjacent to the bone and face each other when the device 1200 is attached to the bone. The interior portions further include protrusions 1222 (similar to protrusions shown in FIGS. 1-11) that are configured to prevent slippage of the plates 1202 when the latter are attached to the bone.

FIGS. 26-27 illustrate parts 1210 and 1212, respectively, of the plates 1202, 1204. Referring to FIG. 26, the part 1210 includes an opening 2610 for insertion of the screw 1220 (not shown), and a plurality of protrusions 1222 disposed on an interior portion of the part 1210. The part 1210 also includes a hollow interior 2616 that is configured to accommodate placement of an extended portion 2714 of the part 1212 (shown in FIG. 27). The part 1210 also includes an opening 2614 configured to accommodate insertion of the screw 1218 for securing the parts 1210 and 1212 together. In some embodiments, the interior portion 2616 can include rail(s) that are configured to mate with corresponding rail(s) of the extended portion 2714 of the part 1212 to allow for smoother sliding of the extended portion 2714 inside the interior portion 2616. The part 1210 further includes a slot 2618 that is configured to accommodate insertion of a locking clip 2512 (shown in FIG. 25). The slot 2618 is configured to include locking flanges 2715 (better shown in FIG. 27) for interlocking the locking clip 2512. The locking clip 2512 is configured to provide additional security to the screw 1218 (shown in FIG. 24).

Referring to FIG. 25, the clip 2512 includes an opening 2516 that is configured to accommodate placement of the screw 1218. In some embodiments, the opening 2516 can be configured to include threads that are configured to correspond to allow a threaded engagement of the screw 1220 to the clip 2512. The clip 2512 further includes a locking spring 2514 that is configured to interact with the flanges 2715 of the slots 2618 (shown in FIG. 26) and 2718 (shown in FIG. 27) and snap into place, once the clip 2512 is inserted into slots 2618, 2718. The openings 2516 of the clip 2512 is configured to align with the openings 2610, 2714 of the respective parts 1210, 1212.

Referring to FIG. 27, the part 1212 is illustrated. The part 1212 is similar to the part 1210, except that it includes the extended portion 2714 that is configured to be inserted into the interior portion 2612 of the part 1210. The extended portion 2714 may also includes ridges 2717 that are configured to interact with the locking screw 1218 in order to secure a particular distance between the parts 1210 and 1212.

Figure 13:
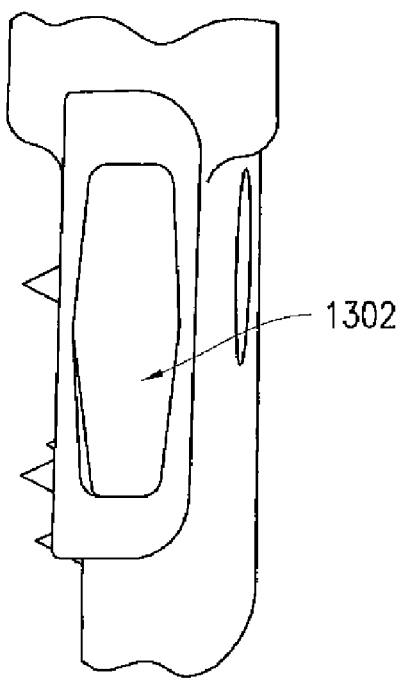
Figure 17:
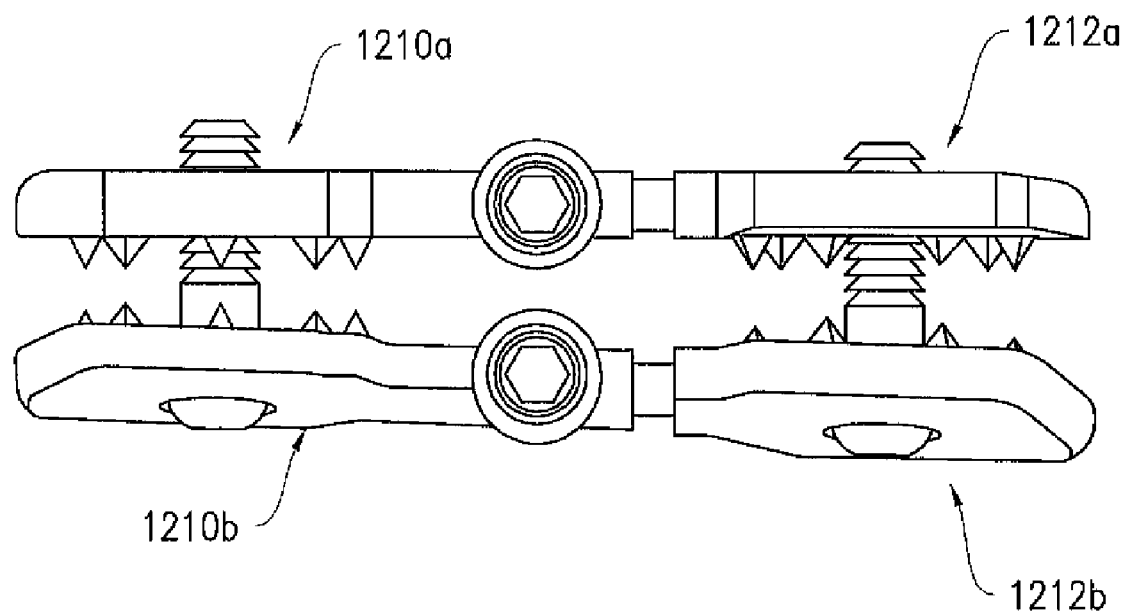
Figure 18:
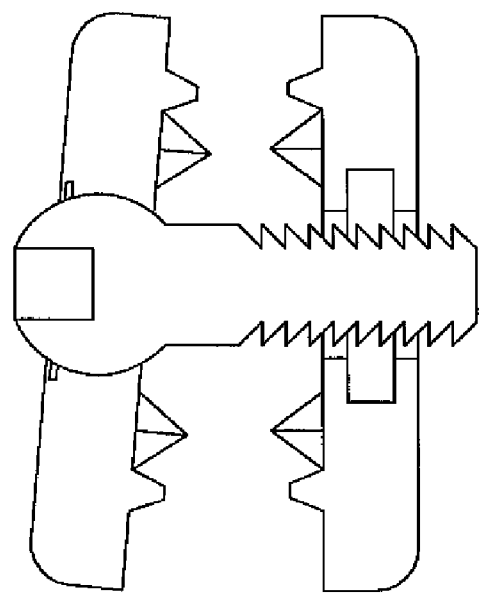
Figure 19:
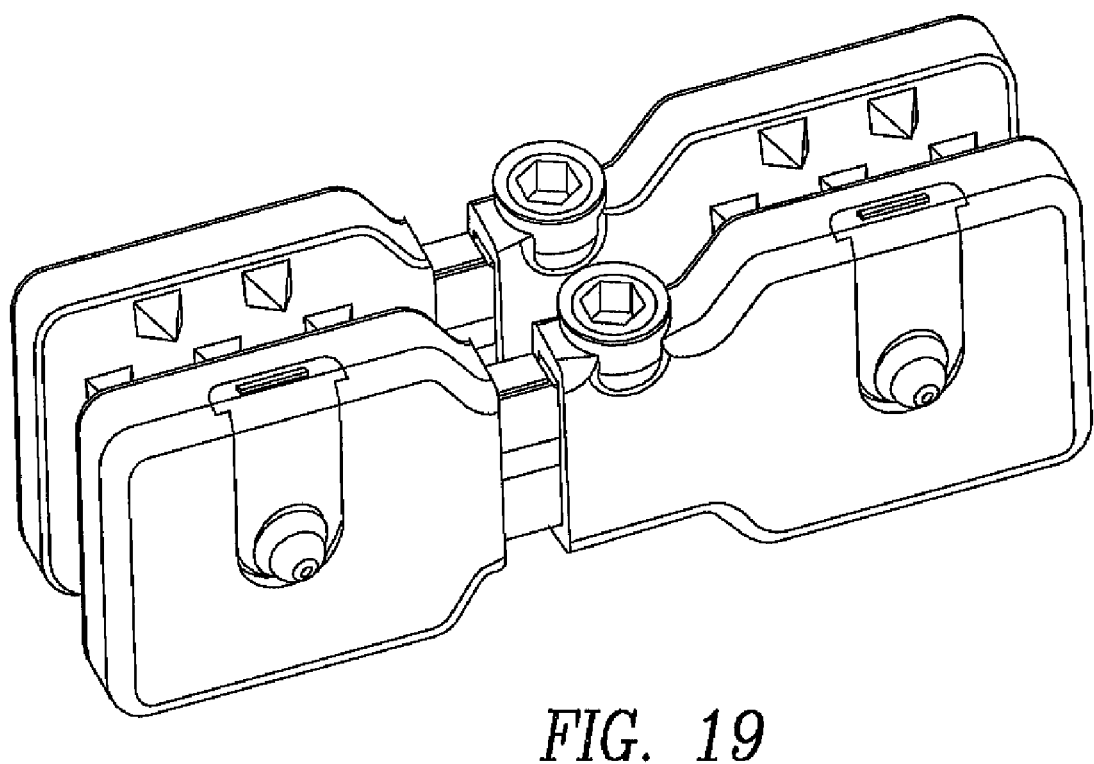
Figure 20:
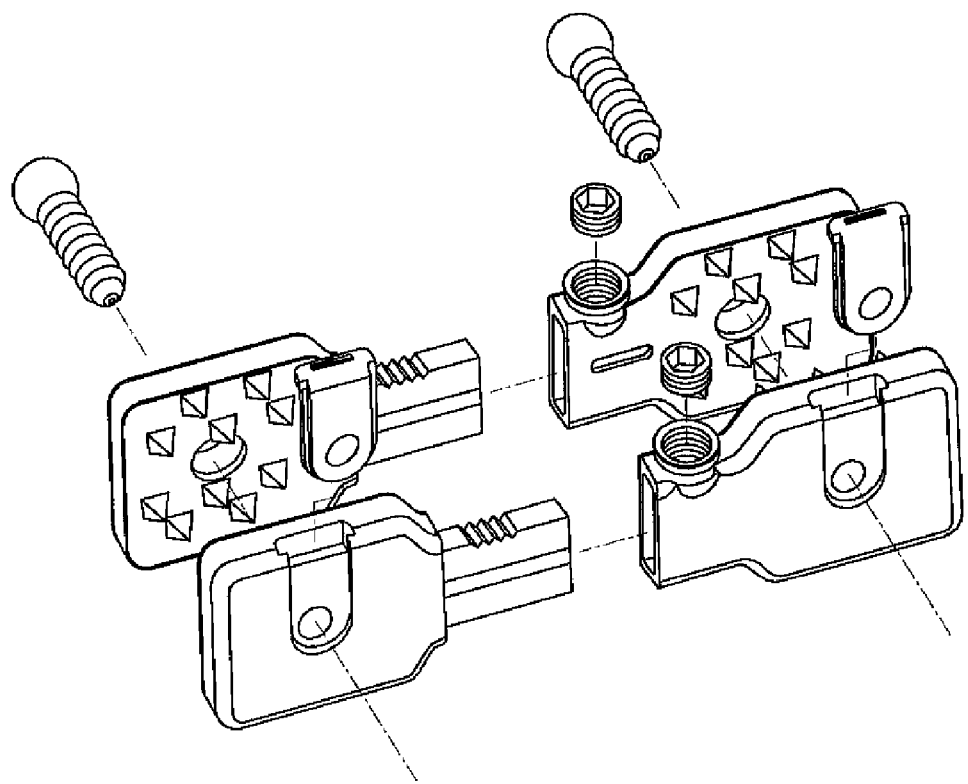
Figure 21:
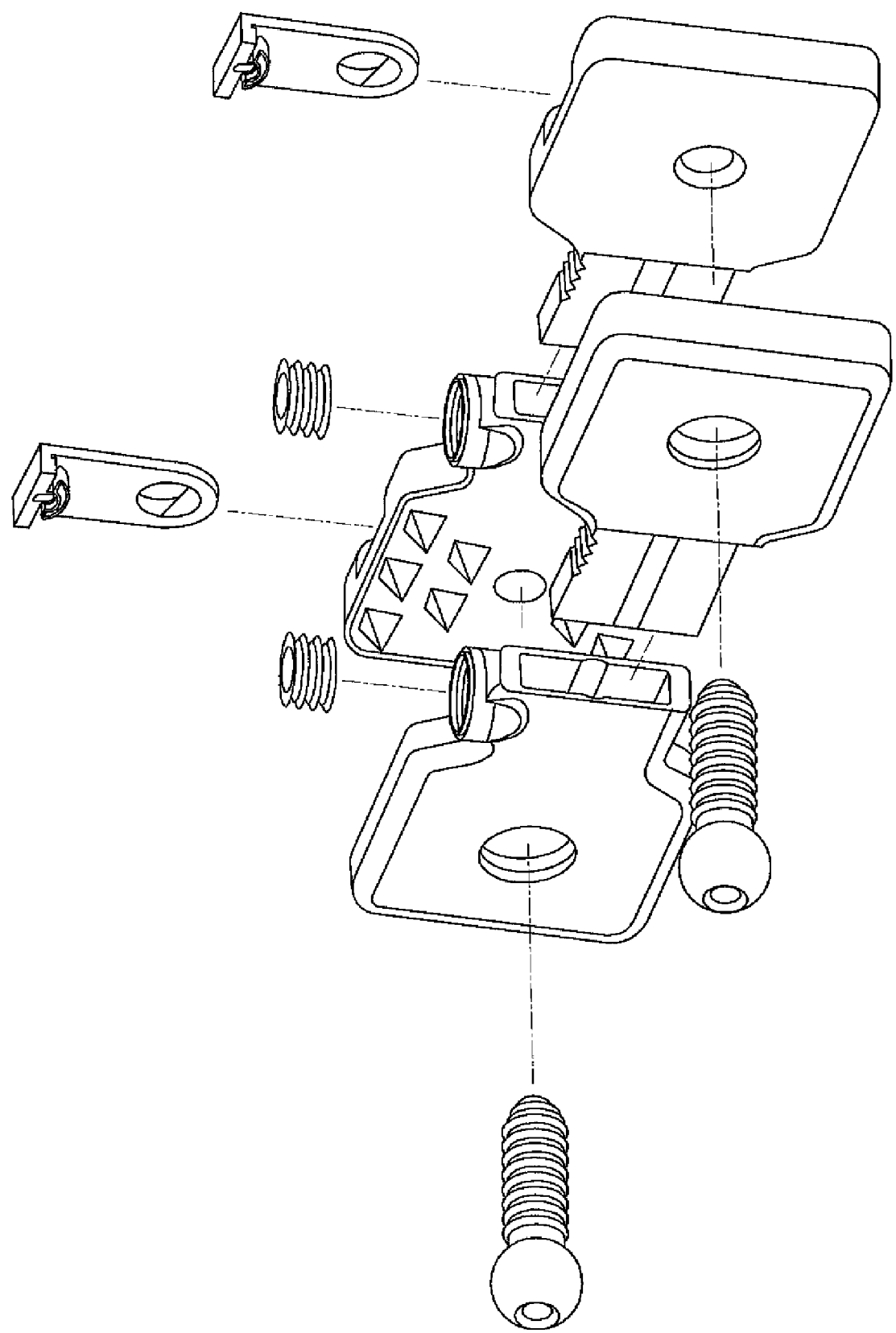
Figure 22:
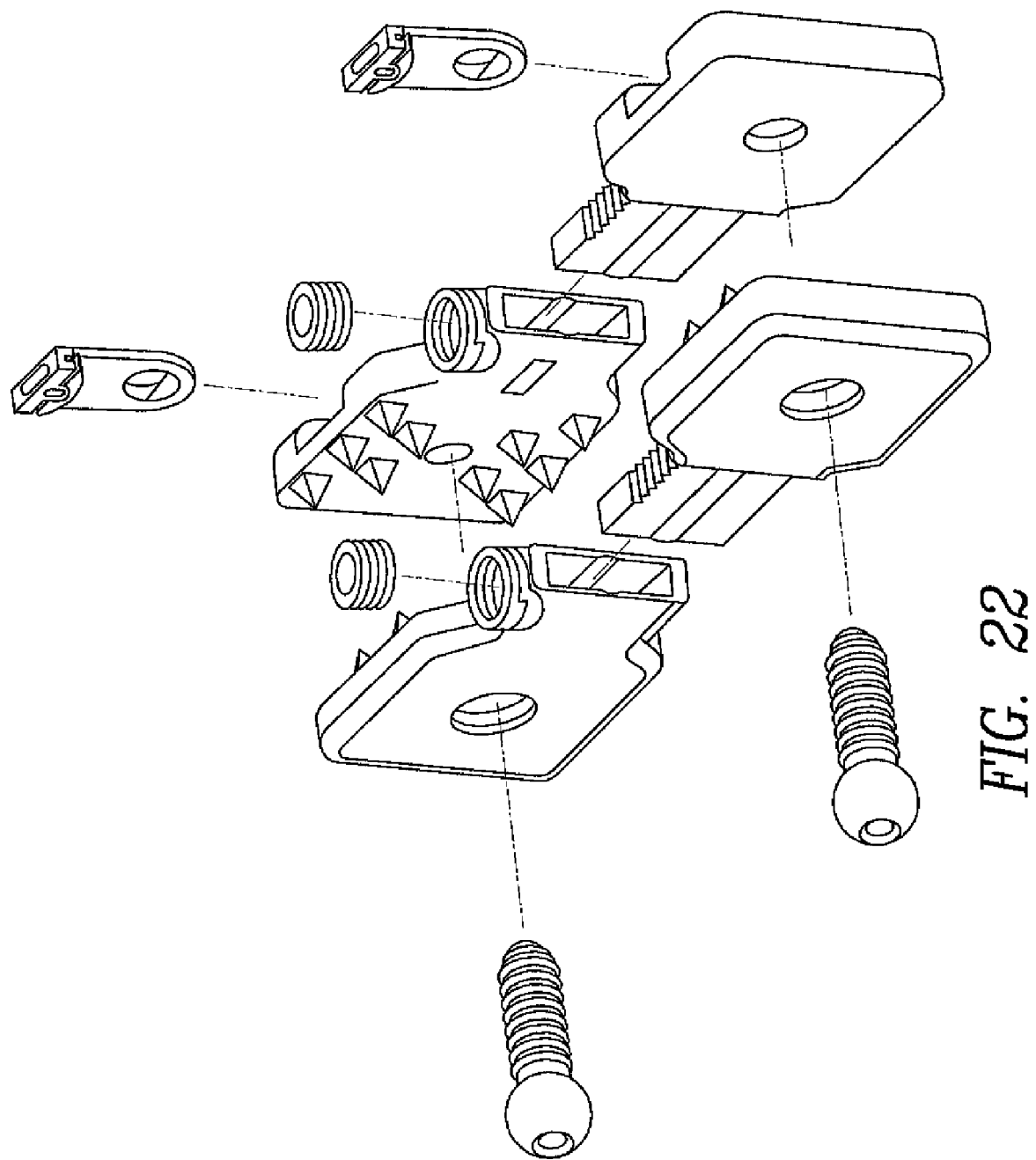
Figure 23:
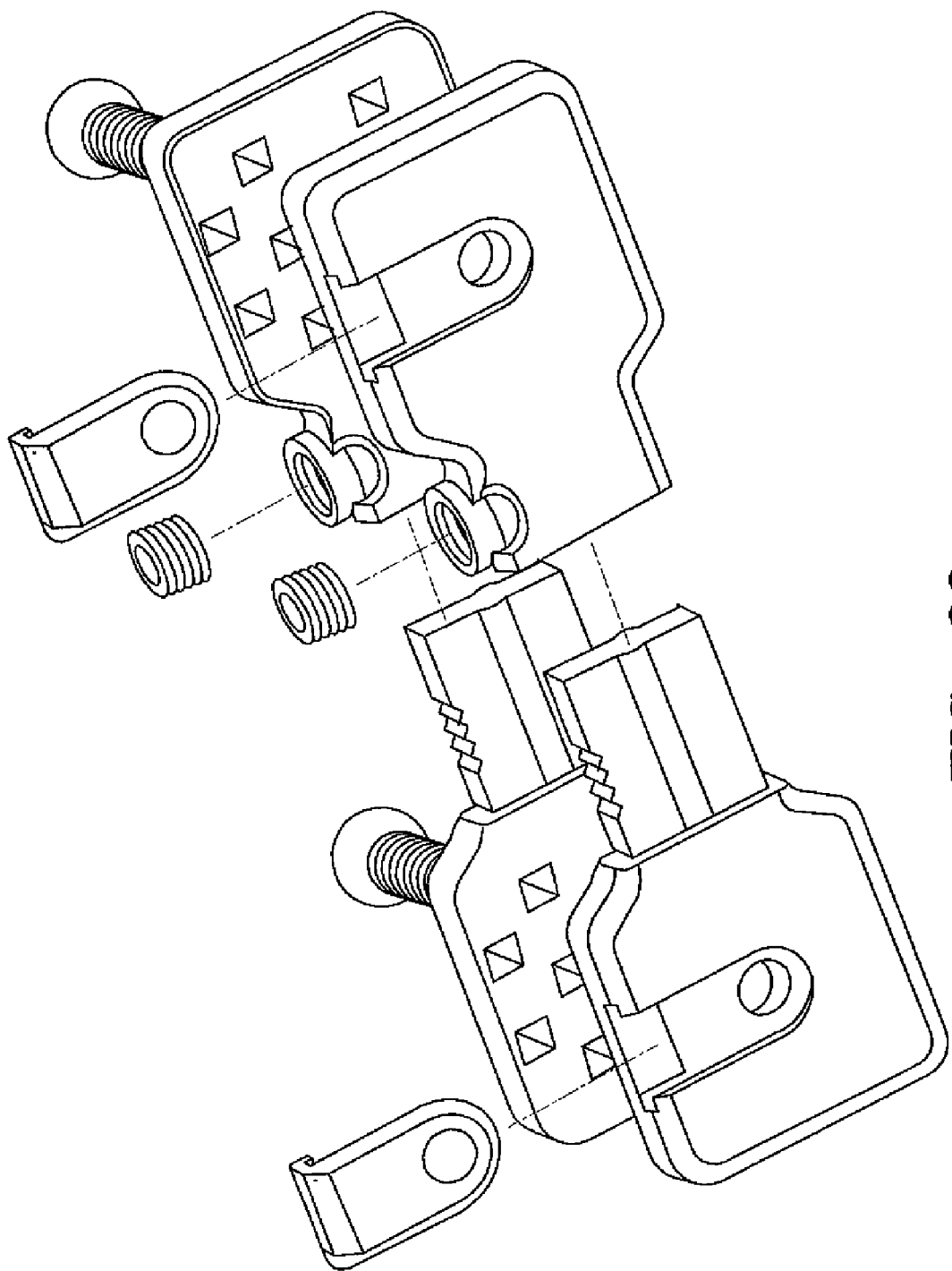

FIGS. 19-23 illustrate various perspective assembled and exploded views of the device 1200. As illustrated, the plates 1202 are coupled together using screws 1220 and clips 2512. The distances between parts 1210 and 1212 are configured to be adjusted using translational mechanisms and screws 1218, as shown and described in FIGS. 26-27. In some embodiments, the plates 1202 are further configured to be disposed at an angle with regard to each other. This means that at least a portion of one plate 1202 can be disposed closer to at least a portion of another plate 1202, as shown in FIGS. 14-18. In some embodiments, such angular displacement is accomplished when the first part 1210*b* and second part 1212*b* of plate 1202*b* are rotatably coupled to a head of the screws 1220*a*, 1220*b*, which allows pivoting of the plate 1202*b* about the head of the screw 1220 (as shown in FIGS. 14 and 17). In some embodiments, such angular displacement is accomplished via placement of an angulation block 1302 (as shown in FIG. 13) that allows pivoting of the plates 1202 about a head of the screw 1220, once the screw 1220 is inserted through the openings 2610, 2714 in the plates 1202. The block 1302 is inserted into one or both of the parts 1210, 1212 around the openings 2610, 2714 and allows for pivotal motion of the plates with respect to each other. In some embodiments, the angulation of the plates 1202 can be between 15 degrees to 30 degrees. Angular disposition of the plates 1202 with respect to each other allows accommodation of various anatomies. The installation process of the device 1200 is similar to the installation process of the devices described above with regard to FIGS. 1-11.

Figure 29:
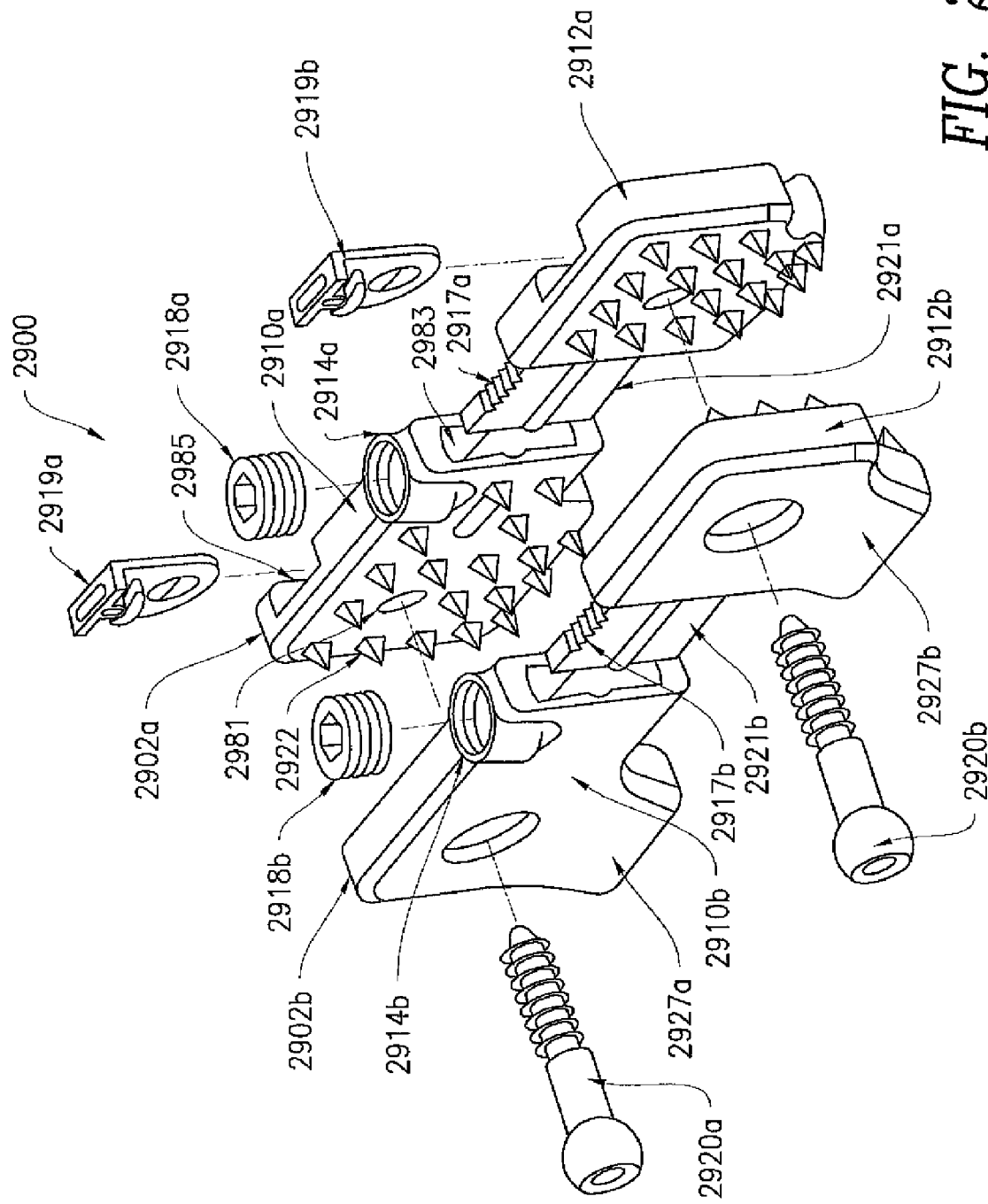
FIG. 29 is an exploded view of another exemplary spinous process clamp having a curved flange for mating to at least a portion of a spinous process, according to some embodiments of the present invention.

FIG. 29 is an exploded view of another example spinous process device 2900, according to some embodiments of the present invention. The device 2900 is similar to the device 1200 shown in FIGS. 12-27. The device 2900 includes a first plate 2902*a* and a second plate 2902*b* that are coupled to each other via connecting screws/bolts/devices 2920*a*, 2920*b*. In some embodiments, the plates 2902 can be angularly coupled to each other. Each plate 2902(*a*, b) is configured to include sliding parts 2910(*a*, b) and 2912(*a*, b), respectively. The parts 2910 and 2912 are configured to be translationally coupled in the mid-section of the plates 2902, thereby allow adjustment of distance between the connecting devices 2920. To secure a particular distance between the connecting devices 2920, each of the plates 2902 includes a securing screw 2918(*a*, b), respectively. This arrangement is similar to the one shown in FIGS. 12-27. In some embodiments, a portion of the part 2910 is configured to fit inside an interior of at least a portion of the part 2912 and allow for a translational movement of the parts 2910 and 2912 with respect to each other, as shown in FIG. 29. Upon translating the parts to a desired distance, a rotational force is applied to the screw 2918 to secure such distance. Each of the plates 2902 include interior and exterior portions. The interior portions are configured to be placed adjacent to the bone and face each other when the device 2900 is attached to the bone. The interior portions further include protrusions 2922 that are configured to prevent slippage of the plates 2902 when the latter are attached to the bone.

Figure 30A:
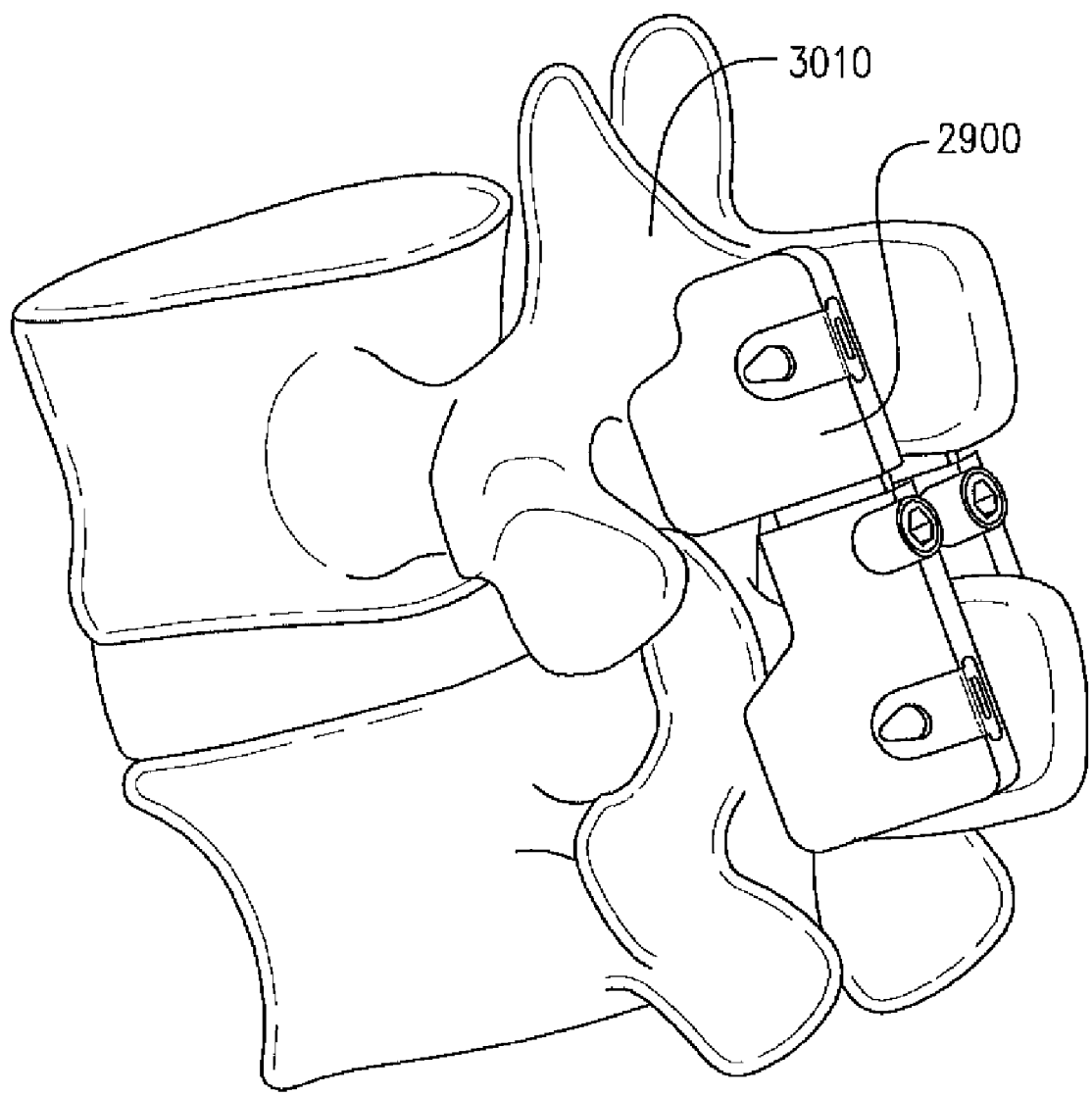
FIGS. 30a-30c illustrate the spinous process clamp shown in FIG. 29 coupled to the spinous process.
Figure 30B:
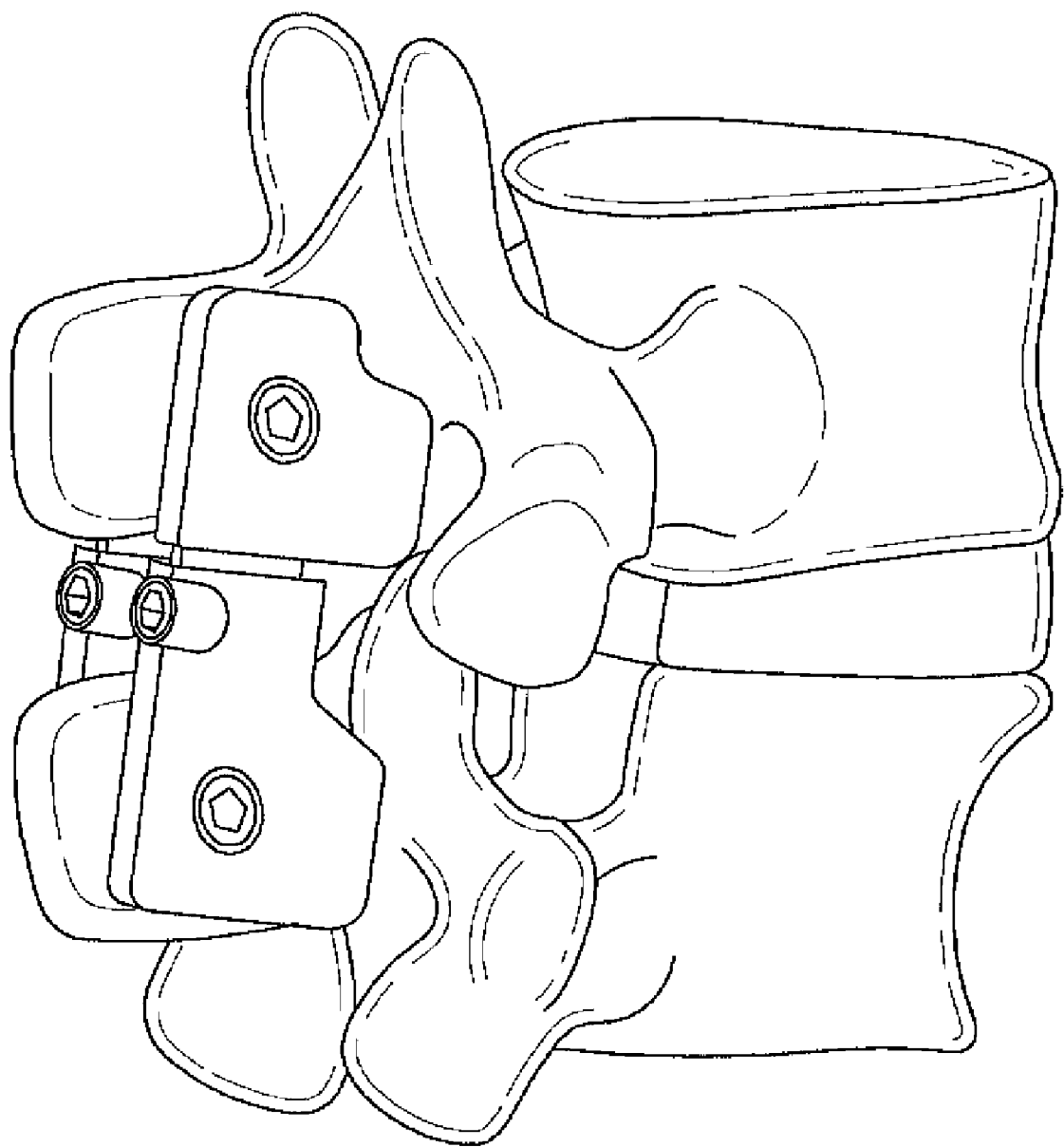
Figure 30C:
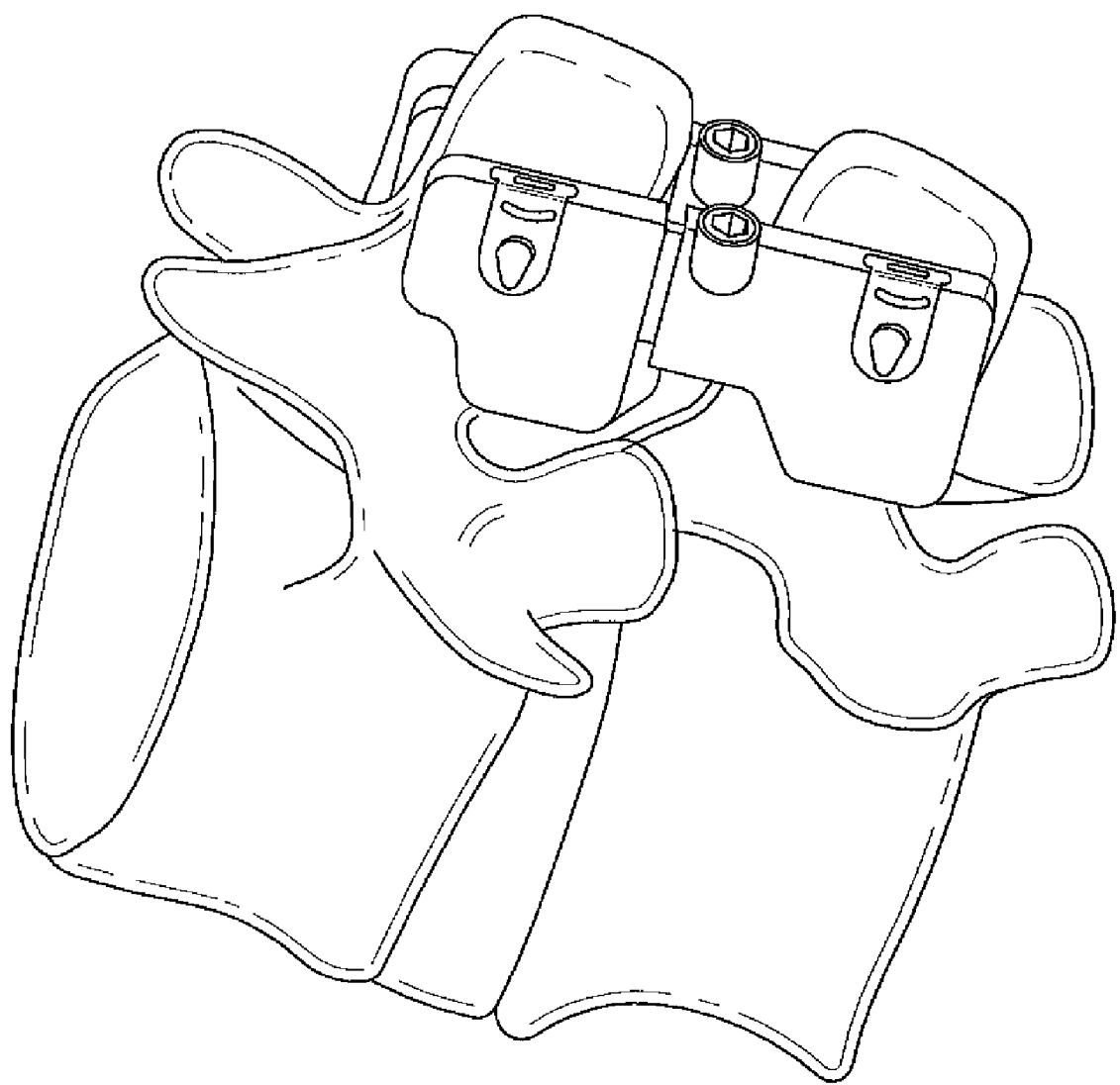

In some embodiments, portions 2910 and 2912 include flange portions 2927(*a*, b), as shown in the plate 2902*b*, wherein the flange portions 2927 are disposed adjacent the bottom parts of portions 2910*b* and 2912*b* of the plate 2902*b*. As can be understood by one skilled in the art, the flange portions 2927 can be configured to be disposed on any or all portions of the plates 2902. The flange portions 2927 are configured to form an angular arrangement with the surfaces of the portions 2910 and 2912, as shown in FIG. 29. Such angular arrangement allows the plates 2902 to firmly grip, hug or otherwise attach to the spinous process' stronger portions, thereby providing additional support to the spinous process plate clamp 2900 when it is secured to the spinous process. The flange portions 2927 can be configured to create additional friction and thus prevent sliding of the plate clamp. In some embodiments, the inner sides of the flange portions 2927 can be configured to include protrusions 2922 (similar to the inner sides of the parts 2910 and 2912), thereby creating further support to the plate clamp 2900. FIGS. 30*a*-30*c* are perspective views of the plate clamp 2900 being attached to spinous process 3010. As can be understood by one skilled in the art, the flange portion 2927 can be configured to form any predetermined angle with the appropriate parts of plates 2902. Such angles can vary from part to part and can be determined by the surgeon (or any other medical professional).

As in the embodiments discussed in connection with FIGS. 12-27 above, the part 2910 includes an opening 2981 for insertion of the screw 2920, and a plurality of protrusions 2922 disposed on an interior portion of the part 2910. The part 2910 also includes a hollow interior 2983 that is configured to accommodate placement of an extended portion 2921 of the part 2912. The part 2910 also includes an opening 2914 configured to accommodate insertion of the screw 2918 for securing the parts 2910 and 2912 together. In some embodiments, the interior portion 2983 can include rail(s) that are configured to mate with corresponding rail(s) of the extended portion 2921 of the part 2912 to allow for smoother sliding of the extended portion 2921 inside the interior portion 2983. The part 2910 further includes a slot 2985 that is configured to accommodate insertion of a locking clip 2919. The slot 2985 is configured to include locking flanges for interlocking the locking clip 2919. The locking clip 2919 is configured to provide additional security to the screw 2918.

Figure 31:
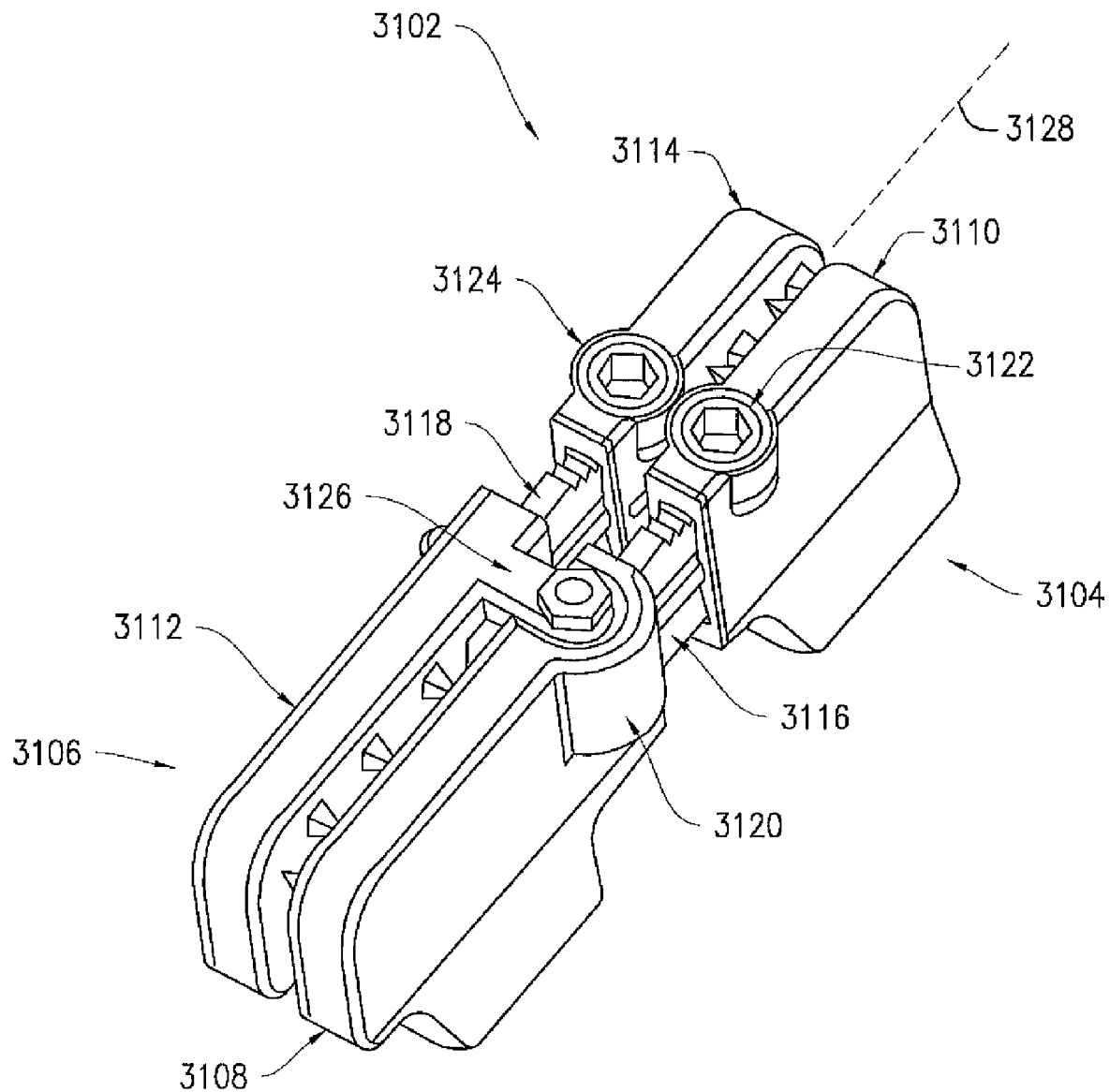
FIG. 31 illustrates a perspective view of a spinous process clamp according to another embodiment for mating to at least a portion of a spinous process.

FIG. 31 illustrates yet another exemplary spinous process clamp device 3102, for fixedly coupling adjacent spinous processes, according to some embodiments of the present invention. The device 3102 is configured to incorporate some of the features of the devices described above with regard to FIGS. 1-30*c*. The spinous process clamp includes a first plate 3104 and a second plate 3106 angularly, rotationally, and translatingly coupled together and configured to abut the opposing bony matter surfaces of adjacent spinous processes. The first plate 3104 and the second plate 3106 share a common longitudinal axis 3128 when in a nominal position. A nominal position may be established by both sliding plates being arranged parallel and adjacent to each other in an elongate longitudinal orientation, prior to conforming to a patient user's spinous process geometry. The longitudinal axis 3128 is substantially parallel with the vertebral axis in the superior-inferior direction of the spine, and substantially located on a plane extending from a medial-lateral anterior location of the spine to a medial-lateral posterior location of the spine. The anterior-posterior plane containing the longitudinal axis 3128 generally aligns with the sagittal plane of the human body.

Referring to FIG. 31, the first plate 3104 includes a first sliding part 3108, a second sliding part 3110, and a securing mechanism or first securing screw 3122, where the first sliding part 3108 is coupled to the second sliding part 3110 and the first securing screw 3122 engages both the first sliding part 3108 and the second sliding part 3110.

Referring to FIGS. 31 thru 33*a-b*, the first sliding part 3108 includes an interior portion 3208 which may have a flat surface configured to abut against one side of a first spinous process, an exterior portion 3206, at least one and a plurality of protrusions 3220 on the interior portion 3208, a pocket 3120, a rod 3204, a first extended portion 3116, at least one ridge 3202, a first flange portion 3214, and a first pivot axis 3314.

In some embodiments, referring again to FIGS. 33*a-b*, the first sliding part 3108 is configured in a generally rectangular or polygonal shape, elongated along the longitudinal axis 3128, or in the superior-inferior direction. The first sliding part 3108 further includes four peripheral surfaces, a first anterior face 3302, a first posterior face 3304, a first coupling face 3308, and a first end face 3306.

In some embodiments, the first anterior face 3302 establishes the furthest-most anterior surface of the first sliding part 3108 relative to the insertion orientation on the spinous processes. In a similar fashion, the first posterior face 3304 establishes the furthest-most posterior surface. The first end face 3306 establishes a length-wise end surface of the first sliding part 3108 and the first plate 3104 when the first and second sliding parts 3108, 3110 are coupled together, and may be considered a lower end of the first sliding part 3108 and first plate 3104. The first coupling face 3308 establishes the length-wise end surface of the first sliding part 3108, and may be considered the upper end of the first sliding part 3108. The opposing peripheral faces 3302, 3304 and 3306, 3308 are generally parallel to each other; however the angular relationship of the opposing faces may vary as dictated by insertion application requirements.

In some embodiments, the interior portion 3208 and the exterior portion 3206 are substantially parallel and substantially flat, however surface geometry may alternatively vary to accommodate further capabilities in the insertion, assembly, location and orientation of the spinous process clamp to a variety of abutting spinous process surfaces, e.g., a surface or cross-section that is curved, wavy, sinusoidal, stepped, angled, thick, thin, or the like. In some embodiments, for example, the first flange 3214 is not flat on the interior and/or exterior portions 3208, 3206. The interior and exterior portions establish the thickness of the first sliding part 3108. The interior portion 3208 is configured to be placed adjacent the bone and face each other when the device 3102 is attached to the bone.

In some embodiments, the interior portion 3208 of the first sliding part 3108 is substantially parallel to the longitudinal axis of the spinous process clamping device when in a nominal position prior to altering the first plate 3104 angular relationship to accommodate spinous processes geometries. The nominal position may subsequently be varied during the course of insertion and abutment to the spinous processes as an intended clamping device feature to accommodate varying geometry of the spinous processes, the application needs of the user, and the surgeon's desired approach to fixation.

The interior portion 3208 of the first sliding part 3108 is configured to include at least one protrusion 3220 coupled to a first bony matter contacting area 3310 of the interior portion 3208 of the first sliding part 3108. The first bony matter contacting area 3310 is configured to directly interact and engage the spinous process. The protrusions 3220 advantageously provide increased frictional contact with bony matter of the spinous processes, mitigating movement by preventing slippage of the first sliding part 3108, the first plate 3104, and the spinous process clamping device relative the spinous process, as well as promoting bone growth attachment to the clamping device, after being securely abutted to adjacent spinous processes. The protrusion may be configured similar to the protrusions of the above devices shown in FIGS. 1-30*c*. The protrusions size and shape may vary depending on the desired application of the spinous process clamp, e.g., height, effective diameter, or the like, and shapes such as pyramidal, cylindrical, conical, frusto-conical, or the like. The variations of size and shape accommodate the specific geometry of the spinous process of the patient user or a desired mechanical interface to the spinous processes.

Figure 33A:
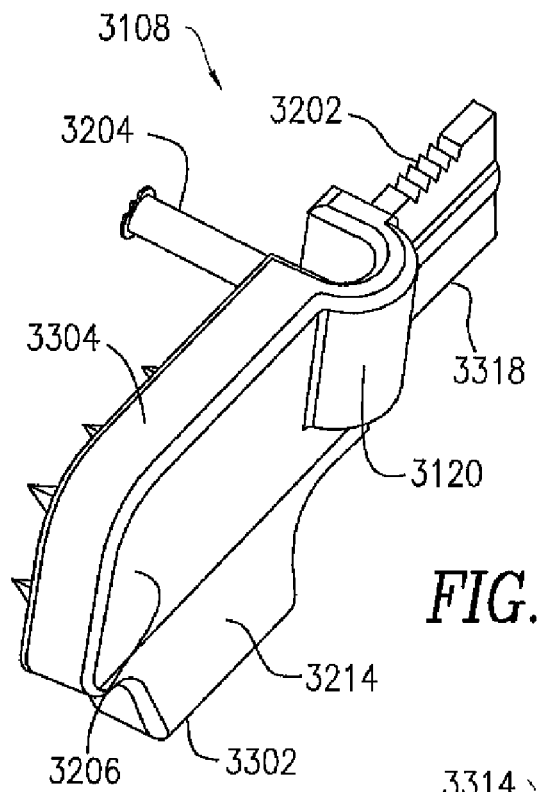
FIGS. 33a-33b illustrate perspective views of a first sliding part, or member, of the spinous process clamp of FIG. 31.
Figure 33B:
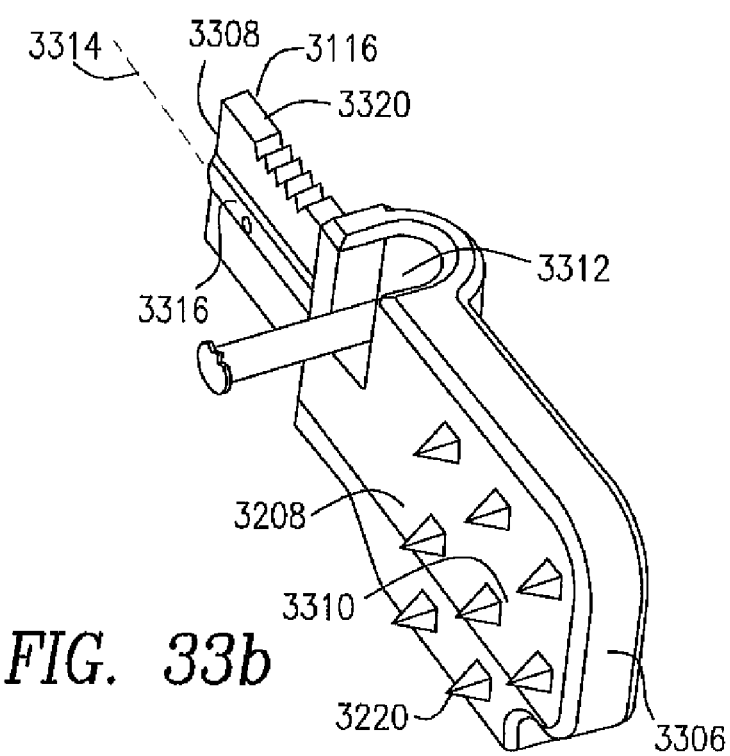

In some embodiments, referring further to FIGS. 33*a-b*, the first sliding part 3108 further includes a first extended portion 3116 extending in a direction along the longitudinal axis away from the first end face 3306 in the superior direction, or alternatively the inferior direction depending on the interchangeable insertion orientation of the clamping device itself, i.e., which end is up as determined by insertion orientation in the body. The first extended portion 3116 further includes a first extended anterior face 3318 and a first extended posterior face 3320, which combine with the first coupling face 3306 to establish the peripheral surfaces of the first extended portion 3116. The first extended portion 3116 may have a rectangular plate-like configuration, and include the first pivot axis 3314 that is generally parallel to the elongate longitudinal axis of the clamping device, but may be varied as necessary. The first extended portion 3116 also has at least one ridge 3202 located on the first extended posterior face 3320, generally containing a plurality of ridges 3202, to provide for adjustability during coupling of the first sliding plate to the second sliding plate as described further below.

In some embodiments, the first extended portion 3116 of the first sliding part 3108 may be configured to include a different surface geometry and medial-lateral cross-section than the interior portion 3208 and the first bony matter contacting area 3310. By way of example, the cross-section geometry of the first extended portion 3116 may be in the shape of a rectangle, a diamond, or a similar polygonal, or circular/rounded shape, or the like. The first extended portion 3116 may have a smaller cross-section than the first bony matter contacting area 3310 portion of the first sliding part 3108 to allow for an insertion coupling into the second sliding part 3110.

In some embodiments, the first sliding part 3108 and the second sliding part 3110 are configured to allow relative motion, rotation or twist, between the two sliding parts about the rotation of axis established on the first sliding part 3108. The first extended portion 3116 may be configured to include the first pivot axis 3314 about which a first pivot surface 3316 is located on the opposing exterior and interior portion surfaces 3206, 3208 of the first extended portion 3116. The first pivot surface 3316 includes geometric features, which may be flat, protrude outward, or be recessed inward, and creating contact/pivot surfaces with the coupling surface of the second sliding part 3110. The geometry of the first pivot surface 3316 may create a discontinuous surface, or shape, on the first extended portion 3116 of the first sliding part 3108, e.g. a semi-cylinder, triangle, rectangle, polygon, or the like. In the embodiment illustrated, the first pivot surface 3316 includes a rounded protrusion extending longitudinally along the first extended portion 3116, provided on both interior and exterior sides of the extended portion 3116, and substantially centered between the first extended anterior and posterior faces 3318, 3320. The rotation or twist capability advantageously allows the two parts 3108, 3110, or ends, of the first plate 3104 to independently conform to the geometry of the engaged spinous process bony matter.

In some embodiments, the first pivot surface 3316 is proximately located at the anterior-posterior midpoint of the first extended portion 3116, between the first extended anterior face 3318 and the first extended posterior face 3320, and extending along at least a portion of the longitudinal direction of the first extended portion 3116. Alternatively, the first pivot surface 3316 may be located anywhere between the first extended anterior face 3318 and the first extended posterior face 3320 and extend in any direction.

In some embodiments, referring again to FIGS. 33a-b, the pocket 3120 includes a recess 3312 in the interior portion 3208 of the first sliding part 3108. The recess 3312 extends transversely to the longitudinal axis of the first sliding part 3108, from the first posterior face 3304 to a distance from the first posterior face 3304. Alternatively, the recess 3312 may be located, beginning and ending, anywhere within the anterior-posterior width of the first sliding plate. The pocket 3120 establishes an open space or recess on the interior portion 3208 configured to receive a portion of the second plate 3106, described below. The pocket 3120 is longitudinally located between the first bony matter contacting area 3310 and the first extended portion 3116 of the first sliding plate. The pocket 3120 is further configured to be located between the adjacent spinous processes, allowing the first plate 3104 and the second plate 3106 to couple between the spinous processes without altering the spinous processes.

The surface of the pocket 3120 is recessed below the surface of the bony matter contacting area 3310 of the first sliding plate and may further recess in an exterior direction beyond the exterior portion 3206 face of the first sliding part 3108. The pocket 3120 may protrude in an exteriorly outward direction to allow the recess 3312 surface to be recessed below both of the planar surfaces of the interior and exterior portions 3208, 3206. Thus, the interior portion 3208 of the pocket 3120 is located a distance between the interior portion 3208 and exterior portion 3206 of the first sliding plate. The longitudinal cross-section of the pocket 3120, transverse to the direction of the pocket 3120 extension, is shaped according to the needs of the user and/or the configuration of the second plate 3106, e.g., a cylinder, a sphere, a polygon, or the like.

In some embodiments, the rod 3204 is fixedly coupled to the interior portion 3208 of the first sliding part 3108 and extends from the interior portion 3208 in a transverse, or orthogonal, direction to the face of the interior portion 3208, and transverse to the longitudinal axis of the first sliding plate. The rod 3204, as illustrated, may also be coupled to the first sliding plate at the pocket 3120. The rod 3204 coupling is located within the thickness of the first sliding part 3108 at the recessed surface of the pocket 3120. The rod 3204 extends a distance sufficient to interact with the second plate 3106 as described below. The rod 3204 length is established by the geometry of the spinous processes and the needs of the patient user.

The rod 3204 as illustrated is longitudinally located substantially in the center of the pocket 3120. In the anterior-posterior direction, the rod 3204 location is a distance from the first posterior face 3304 of the first sliding plate, and is configured to couple to the coupling means of the second plate 3106 as described below. The rod 3204 is located anterior to the coupling element, or arm 3126, of the second plate 3106. Additionally, the rod 3204 is configured to be located between the adjacent spinous processes.

In some embodiments, the ridges 3202 are located on the first extended posterior face 3320 of the first extended portion 3116 of the first sliding part 3108. The ridges 3202 form a discontinuous surface on the first posterior face. The discontinuous, or non-flat, geometric features can be of varying shapes e.g., polygon-shaped steps, curves, sinusoidal, triangular, or the like. The shape of the ridges 3202 extend transverse, or orthogonal, to the longitudinal axis of the first sliding plate and substantially orthogonal to the exterior portion 3206 and the interior portion 3208. Alternatively, the direction and shape of the discontinuous ridges 3202 can be in any desired orientation or shape. The discontinuous surface extends along the full thickness of the first extended portion 3116 between the interior and exterior portions 3208, 3206, or alternatively, along a sufficient portion to engage the securing screw 3122 as discussed below.

The ridges' 3202 surface geometry discontinuity provides a friction inducing or locking location to establish a securing force by means of the securing screw 3122 when the spinous process clamping device is assembled. Assembly for the ridges 3202 occurs when the first sliding part 3108, the second sliding part 3110, and the securing screw 3122 are coupled together to form the first plate 3104.

In some embodiments, the first flange portion 3214 is located adjacent the anterior portion of the first sliding part 3108 and extends outwardly from the vertebral center, the longitudinal axis of the spinous process clamping device, and the exterior portion 3206 in an exterior direction. The first flange portion 3214 surface may be rounded around the peripheral surfaces of the first sliding part 3108. The radial degree of rounding at the corners and the edges, and the angular degree of the first flange portion 3214 trajectory away from the longitudinal axis or the interior portion 3208, can be varied. The first flange portion 3214 shape provides for a secure abutment to the spinous processes, and accommodates a variety of patient user spinous process geometries. The first flange portion 3214 geometry is one optional surface feature that makes the interior and exterior portions 3208, 3206 of the first sliding plate non-flat.

Figure 37A:
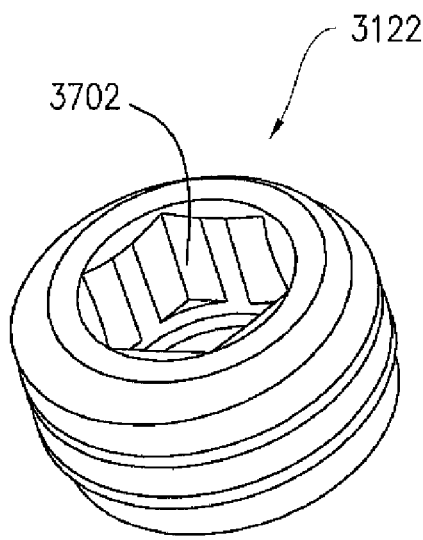
FIGS. 37a-37b illustrate perspective views of a securing screw configured to couple members of the spinous process clamp of FIG. 31.
Figure 37B:
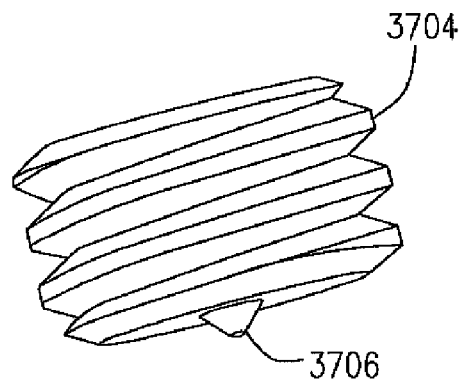

In some embodiments, illustrated in FIGS. 37a-b, the first securing screw 3122 may include a threaded cylinder, or a functional equivalent, that establishes the desired longitudinal length of the first plate 3104 by locking the coupled relationship between the first sliding part 3108 and the second sliding part 3110. The first securing screw 3122 has an endpoint projection 3706 that engages the geometric features of the ridges 3202 and prevents the first extended portion 3116 of the first sliding part 3108 from de-coupling from the second sliding part 3110. The first securing screw 3122 additionally has a recess 3702 configured to accommodate wrenches as described for screw 110 above, to allow installation into the first opening 3210 by rotatingly engaging the threads 3704 of the screw with threads in the opening 3210. Alternatively, other fastening mechanisms known in the art may be used to secure the two sliding parts. The longitudinal length of the first extended portion 3116, and the location of the ridges 3202, may vary according to the patient user needs to establish the overall length of the first plate 3104.

Figure 34A:
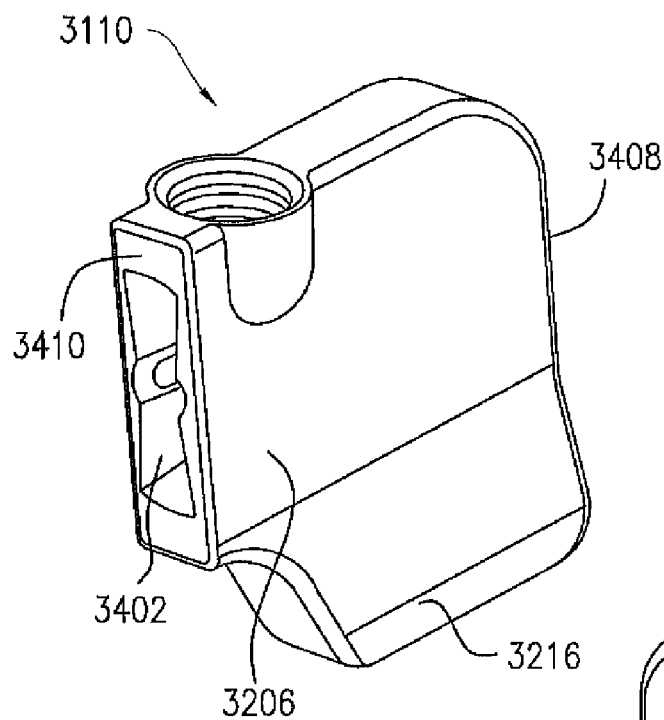
FIGS. 34a-34b illustrate perspective views of a second sliding part, or member, of the spinous process clamp of FIG. 31.
Figure 34B:
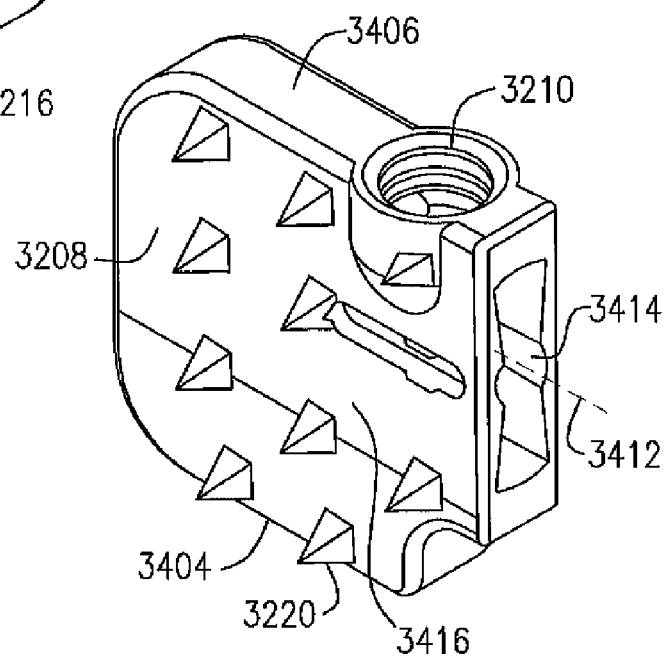
Figures 35A, 35B:
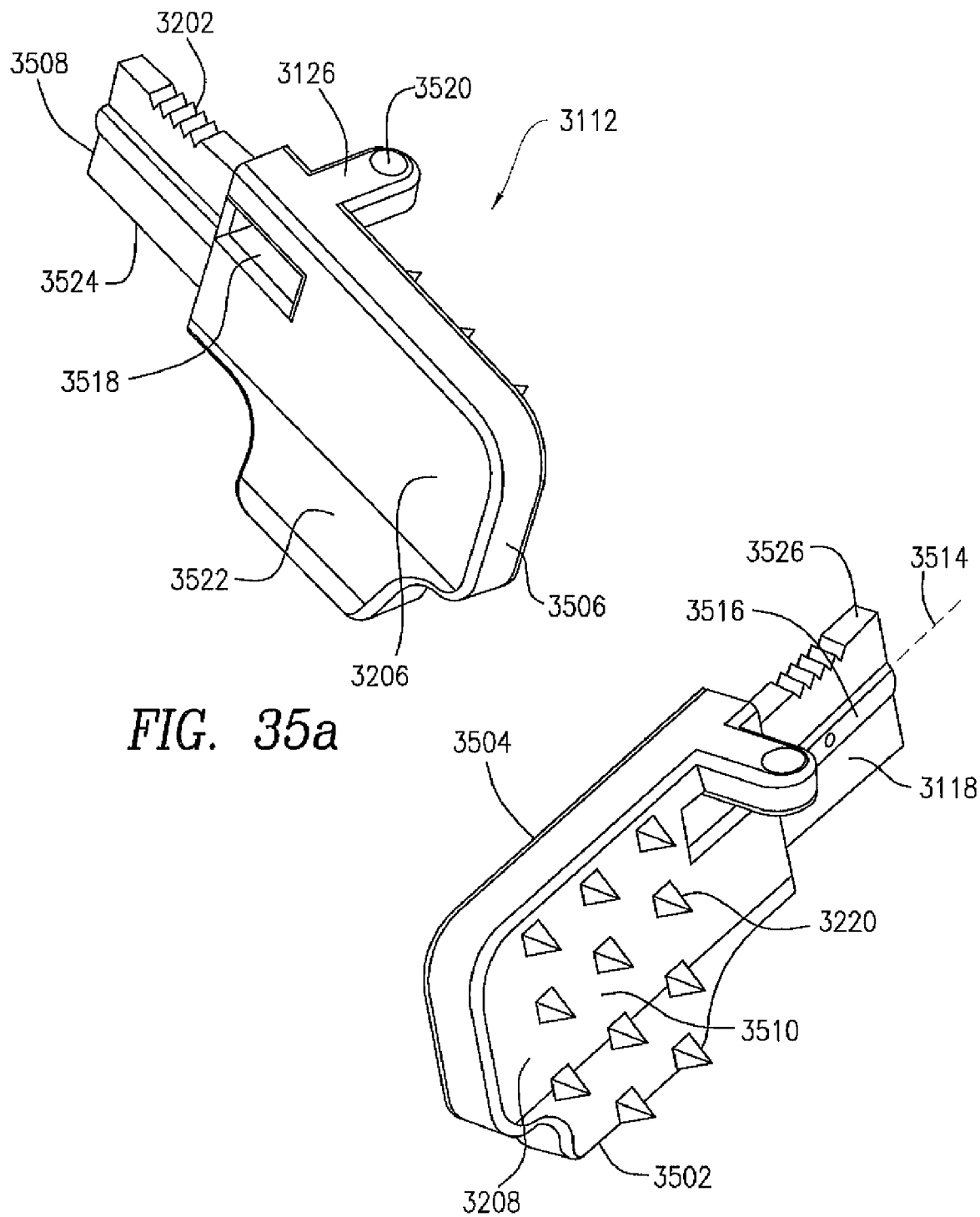
FIGS. 35a-35b illustrate perspective views of a third sliding part, or member, of the spinous process clamp of FIG. 31.

Referring to FIGS. 34a-b, in some embodiments the second sliding part 3110 includes an interior portion 3208, an exterior portion 3206, a first hollow interior 3402, a second pivot axis 3412, a second pivot surface 3414, a second flange portion 3216, at least one protrusion 3220, a second bony matter contacting area 3416, a second anterior face 3404, a second coupling face 3410, a second end face 3408, and a second posterior face 3406. Like named elements include similar characteristics as the first sliding part 3108, and details with respect to such second sliding part 3110 elements are referred to the description of the first sliding part 3108.

In some embodiments, the interior portion 3208, the exterior portion 3206, the peripheral faces 3404, 3406, 3408, 3410, the second bony matter contacting area 3416, and the protrusions 3220 may have the same characteristics as the first sliding part 3108. However, the entire interior portion 3208 of the second sliding part 3110 includes substantially of the second bony matter contacting area 3416 and configured to abut a second adjacent spinous process. Additionally, the second coupling face 3410 of the second sliding part 3110 includes an aperture opening to the first hollow interior 3402.

The parallel relationship between the interior portion 3208 and the exterior portion 3206 of the second sliding part 3110 may be modified to accommodate a patient user's needs upon insertion. Therefore, the two surfaces can have a substantially angled or varying relationship between the exterior and interior portion 3208s. Accordingly, the exterior and interior parallel relationship can also be modified on the first sliding part 3108.

Generally the relationship between the interior portion 3208 and the exterior portion 3206 of both the first sliding part 3108 and the second sliding part 3110 may be similar. However, the relationship between the two surfaces may differ between the first sliding part 3108 and the second sliding part 3110 as required to accommodate insertion into the patient user.

In some embodiments, the second coupling face 3410 is configured to receive the first extended portion 3116 of the first sliding part 3108. The second end face 3408 of the second sliding part 3110 is configured to be opposite the first end face 3306 of the first sliding part 3108 and may be considered the upper end of first plate 3104. The first end face 3306 of the first sliding part 3108 and the second end face 3408 of the second sliding part 3110 establish the outermost longitudinal ends of the first plate 3104 when the first sliding part 3108 and the second sliding part 3110 are coupled together. Thus, they establish the overall length of the first plate 3104.

In some embodiments, the first hollow interior 3402 of the second sliding part 3110 is configured to receive the first extended portion 3116 of the first sliding part 3108. The first hollow interior 3402 includes a second pivot axis 3412 that generally is in the elongate direction and parallel to the longitudinal axis of the spinous process clamping device. However, the second pivot axis 3412 may vary in a manner similar to the first pivot axis 3314 of the first sliding part 3108. The first hollow interior 3402 further includes the second pivot surface 3414 about the second pivot axis 3412 configured to receive the first pivot surface 3316 of the first extended portion 3116 of the first sliding part 3108. Pivot surface 3414 may be rounded or similarly shaped to mate with pivot surface 3316. The two pivot surfaces 3316, 3414 interact when the first sliding part 3108 is coupled to the second sliding part 3110 to allow the first sliding part 3108 and the second sliding part 3110 to rotate, or twist with respect to each other, about the substantially co-linear pivot axes 3314, 3412 of the two sliding parts. The rotation, or twist, is accommodated by the configuring of the first hollow interior 3402 and the first extended portion 3116, allowing the first extended portion 3116 to rotate about the pivot surfaces within the first hollow interior 3402. As illustrated, the first hollow interior 3402 may be configured to define a bow-tie shape opening, which widens from its center toward the posterior and anterior ends, to accommodate rotation of the first extended portion 3116 in first hollow interior 3402 about the pivot surfaces 3316, 3414.

In some embodiments, the first opening 3210 of the second sliding part 3110 is located on the second posterior face 3406 of the second sliding part 3110. The first opening 3210 is threaded and configured to receive the first securing screw 3122. The first opening 3210 is further configured to allow the first securing screw 3122 engaging end 3706 to further engage at least one ridge 3202 of the first extended portion 3116, where the first extended portion 3116 is inserted in first hollow interior 3402. The first opening 3210 location allows access to insert the securing screw 3122, or to secure the securing mechanism, subsequent to insertion of clamping device 3102 into the patient user. Alternatively, the securing screw 3122 may also be secured to the first and second sliding parts 3108, 3110 prior to insertion into the patient user. The opening 3210 is advantageously oriented to provide direct posterior access, as opposed to lateral access, to adjust the first plate 3104 length.

Securing the securing screw 3122 into the first opening 3210 and engaging the ridge 3202 of the first extended portion 3116 establishes a longitudinal relationship between the first sliding part 3108 and the second sliding part 3110 and determines the overall length of the first plate 3104. A plurality of ridges 3202 on the first extended portion 3116 provides adjustability to the overall length of the first plate 3104. The securing screw 3122 may selectively engage a ridge 3202 on the first extended portion 3116 that will most beneficially enable insertion of the spinous process clamping device onto the adjacent spinous processes and into the patient user.

Figure 32:
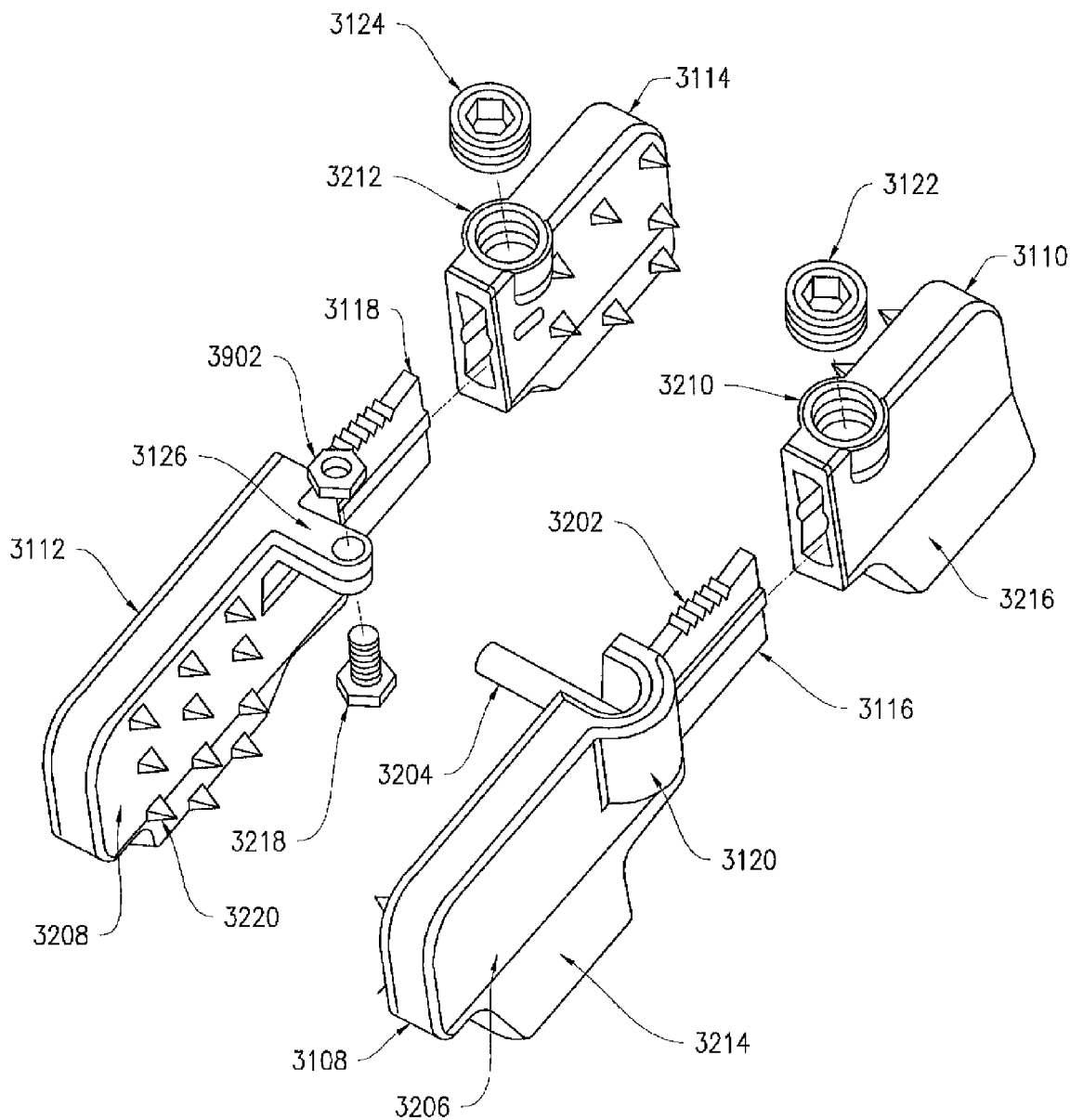
FIG. 32 is an exploded view of the spinous process clamp of FIG. 31 for mating to at least a portion of a spinous process.

Similarly, referring to FIGS. 31 and 32, the second plate 3106 includes a third sliding part 3112, a fourth sliding part 3114, and a second securing screw 3124, where the third sliding part 3112 is coupled to the fourth sliding part 3114 and the second securing screw 3124 engages both the third sliding part 3112 at a second opening 3212, and the fourth sliding part 3114.

In some embodiments, referring to FIGS. 31, 32 and 35*a-b*, the third sliding part 3112 includes an interior portion 3208, an exterior portion 3206, a second extended portion 3118, a third pivot axis 3514, a third pivot surface 3516, at least one ridge 3202, a third flange portion 3522, at least one protrusion 3220, a third bony matter contacting area 3510, an arm 3126, an aperture 3518, a third anterior face 3502, a third coupling face 3508, a third end face 3506, and a third posterior face 3504. The second extended portion 3118 further includes a second extended anterior face 3524 and a second extended posterior face 3526, which combine with the third coupling face 3508 to establish the peripheral surfaces of the second extended portion 3118.

Like named elements include similar characteristics as the first plate 3104 and the first sliding part 3108, and are generally symmetric about the longitudinal axis of the spinous process clamping device. Details with respect to common third sliding part 3112 elements are referred to the description of the first sliding part 3108. The elemental differences between the first sliding part 3108 and the third sliding part 3112 include the aperture 3518 and the arm 3126, and the lack of a rod 3204 and a pocket 3120 on the third sliding part 3112. The common elements of the first sliding part 3108 and the third sliding part 3112 are not required to be symmetric about the longitudinal axis of the clamp; each may vary independently within the scope of the disclosure.

In some embodiments, referring again to FIGS. 35*a-b*, the arm 3126 of the third sliding part 3112 is coupled to the interior portion 3208 and is located adjacent to, and may be a part of, the third posterior face 3504. The arm 3126 extends transversely, or orthogonal to, the longitudinal axis of the clamp device and extends away from the interior portion 3208 of the third sliding part 3112. The arm 3126 extends in the same general direction as the protrusions 3220, away from the third bony matter contacting area 3510. The arm 3126 further has a third opening 3520 at the outward-most end of the arm 3126, the end that extends away from the interior portion 3208 of the third sliding part 3112.

The arm 3126 is generally a polygonal shape, although the shape can be configured in any shape deemed appropriate for insertion into the patient user and abutment to adjacent spinous processes. The arm 3126 has an anterior surface and a posterior surface. The third opening 3520 extends in an anterior-posterior direction, transverse to the longitudinal axis, creating a through-hole between the anterior and posterior surfaces of the arm 3126. The through-hole is configured to receive a clevis 3218 described further below.

In some embodiments, the aperture 3518 is rectangular in shape, and has an elongate direction generally parallel to the longitudinal axis of the third sliding part 3112. The aperture 3518 has a generally polygonal shape, however the aperture 3518 can take the shape of a curved, circular, oval, or non-polygon shape as determined most appropriate for function, costs of manufacturability, or any other variable deemed applicable. The polygonal shape generally has a shorter length in the anterior-posterior axis and a longer elongate length in the superior-inferior direction, or the longitudinal direction of the clamping device.

The aperture 3518 is located adjacent to the anterior side of the arm 3126, spaced a distance from the third posterior face 3504 of the third sliding part 3112. The aperture 3518 extends transversely through the thickness of the third sliding part 3112, extending from the exterior portion 3206 through to the anterior surface of the third sliding part 3112. The aperture 3518 is configured to receive, if necessary, the rod 3204 of the first sliding part 3108 upon assembly and insertion of the first plate 3104 and the second plate 3106 of the spinous process clamping device.

The features and characteristics of the third sliding part 3112 are not necessarily required to be the same as that of the first sliding part 3108. Variations may exist between the geometries, features, and other common characteristics of both the first sliding part 3108 and the third sliding part 3112 as may be necessary to accommodate orientation for insertion at the geometric surfaces of the spinous processes of the patient user.

Figure 36A:
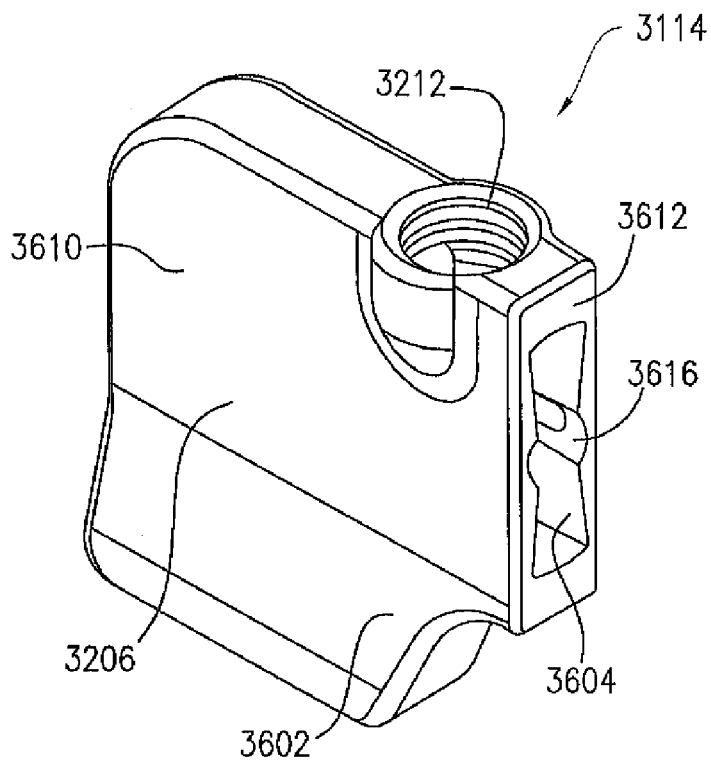
FIGS. 36a-36b illustrate perspective views of a fourth sliding part, or member, of the spinous process clamp of FIG. 31.
Figure 36B:
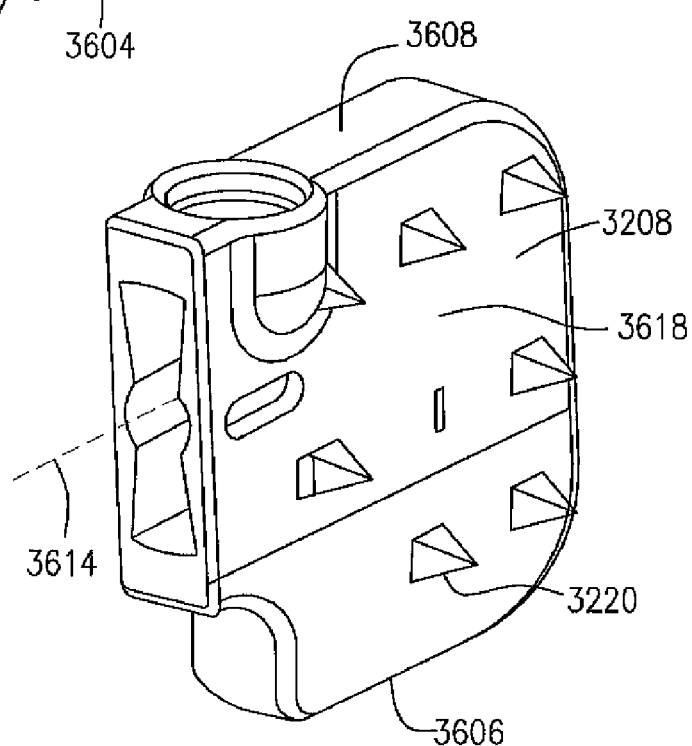

In some embodiments, referring to FIGS. 36*a-b*, the fourth sliding part 3114 includes the same elements, and disclosed variations to those elements, as the second sliding part 3110. The fourth sliding part 3114 includes an interior portion 3208, an exterior portion 3206, a second opening 3212, a second hollow interior 3604, a fourth pivot axis 3614, a fourth pivot surface 3616, a fourth flange portion 3602, at least one protrusion 3220, a fourth bony matter contacting area 3618, a fourth anterior face 3606, a fourth coupling face 3612, a fourth end face 3610, and a fourth posterior face 3608. Like named elements include similar characteristics as the second sliding part 3110, and details with respect to these fourth sliding part 3114 elements are referred to the description of the second sliding part 3110.

The third sliding part 3112 and the fourth sliding part 3114 may be coupled together and provide an ability to rotate, or twist, relative to each part, in a manner similar to the first sliding part 3108 and the second sliding part 3110.

Figure 38:
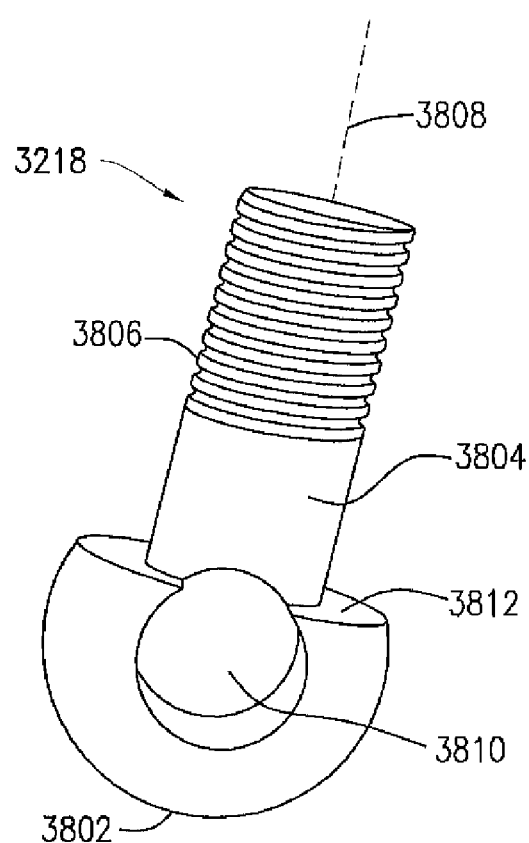
FIG. 38 illustrates a perspective view of a clevis configured to couple members of the spinous process clamp of FIG. 31.
Figure 39:
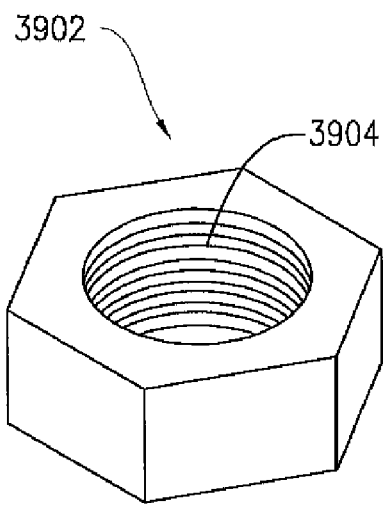
FIG. 39 illustrates a perspective view of a nut configured to couple a clevis and members of the spinous process clamp of FIG. 31.

In some embodiments, the spinous process clamping device further includes the clevis 3218. Referring to FIG. 38, the clevis 3218 includes a rounded, curved, or spherical head 3802, an aperture 3810 through-hole in the head, a shank 3804, and external threads 3806 on a threaded portion of the shank. The clevis 3218 includes a nut 3902, referring to FIG. 39, having internal threads 3904, to engagingly secure on the threaded portion of the shank 3804. The through-hole aperture 3810 has a centerline axis extending through the head of the clevis 3218, and the clevis 3218 aperture 3810 through-hole is configured to receive the rod 3204. The shank has a longitudinal axis 3808 that extends away from the head 3802 in a transverse, or orthogonal, direction to the aperture 3810 through-hole centerline axis. The aperture 3810 through-hole diameter extends further toward the clevis 3218 shank than a flat 3812 of the clevis 3218 head 3802, where the flat 3812 of the head 3802 is substantially orthogonal to the shank longitudinal axis. The clevis 3218 is coupled to the nut 3902 by threading the nut onto the threaded shank.

The spinous process clamping device is coupled together via the clevis 3218 and the arm 3126 of the second plate 3106 and the rod 3204 of the first plate 3104. The clevis 3218 engages the arm 3126 by inserting the clevis 3218 shank 3804 through the third opening 3520 on the arm 3126. The clevis 3218 shank 3804 longitudinal axis 3808 is transverse to the longitudinal axis 3128 of the spinous process clamp device. The nut 3902 is then engaged with the threads 3806 on the shank 3804 to secure the clevis 3218 to the arm 3126 of the second plate 3106, or the third sliding part 3112. The clevis 3218 and second plate 3106 is then secured to the first plate 3104 by aligning the clevis 3218 aperture 3810 though-hole centerline axis with the rod 3204 length-wise axis such that the clevis 3218 receives the rod 3204. The nut 3902 coupling to the clevis 3218 is advantageously located directly posterior to the insertion direction, allowing direct access to the nut 3902 for insertion adjustment and securing of the two plates 3104, 3106.

Securing of the two plates 3104, 3106 occurs by way of rotating the nut 3902 such that the internal threads 3904 of the nut 3902 securingly engage the external threads 3806 of the clevis 3218. The arm 3126 and rod 3204 are tightly secured by means of the flat 3812 on the clevis 3218 being located on a plane projecting through/within the aperture 3810. This means the aperture 3810 extends further on the longitudinal axis 3808 toward the threaded end than the flat 3812. Thus, as the nut 3902 engages clevis 3218 and draws the clevis head 3802 toward arm 3126, the rod 3204 contacts arm 3126 before flat 3812. The rod 3204 contact establishes a physical stop for the clevis 3218 and further engaging rotation of nut 3902 creates a tight securing between arm 3126 and rod 3204 via the clevis 3218 and nut 3902, while flat 3812 does not contact arm 3126.

Prior to securing of the nut 3902, the clevis 3218 can advantageously translate along the length of the rod 3204. The gap, or spaced distance, between the first plate 3104 and the second plate 3106, is varied by the translation of the clevis 3218 on the rod 3204. The gap is modified upon insertion to allow the first and the second plates 3104, 3106 to abut the adjacent spinous processes, which provides for installation on varying thicknesses of spinous processes. The non-incremental translation allows for infinite adjustability between the two plates 3104, 3106. The dynamic coupling of the rod allows compression and distraction without interference with the adjacent spinous structures or anatomy. Additionally, the clevis 3218 can rotate about the shank longitudinal axis 3808 inserted through the arm 3126 third opening 3520. The clevis 3218 rotation allows the first plate 3104 and the second plate 3106 to rotate with respect to each other about the clevis 3218 shank 3804 longitudinal axis 3808. The rotation capability further allows the spinous process clamping device to adjust to the particular geometry of the patient user's spinous processes.

The configuration of the rod 3204 may advantageously vary in length to accommodate a wide variety of thicknesses of the adjacent spinous processes. The rod 3204 may be longer than the lateral thickness of the spinous processes, in which case the end of the rod 3204 projecting through the clevis aperture 3810 may also extend through the aperture 3518 of third sliding part 3112. Additionally, the first and second plates 3104, 3106 can contact at their interior portions 3208, to minimize overall size of clamping device 3102 during insertion, as desired. The elongate shape of aperture 3518 provides for longitudinal movement of the rod 3204 within aperture 3518, which may be desired when the first and second plates rotate with respect to each other about clevis 3218. Thus, the elongate aperture 3518 provides a wide range of rotation between the two plates, further providing ease of insertion, assembly and abutment of the spinous process clamping device 3102 in the patient user.

The spinous process clamping device can advantageously adjust by rotation of the two plates 3104, 3106 with respect to each plate about a variably selected pivot axis established by the clevis 3218 location, and by rotation, or twist of each sliding part 3108, 3110, 3112, 3114 of the two plates 3104, 3106 about the common pivot axis of the extended portions 3116, 3118 and the hollow interiors 3402, 3604. Thus, the spinous process clamping device 3102 provides for an angularly, rotatably, and translatingly capable coupling between the two plates 3104, 3106, as well as independent rotation or twist between the individual parts or members 3108, 3110, 3112, 3114, of each plate 3104, 3106.

The spinous process clamp device 3102 is assembled, inserted, and abutted against adjacent spinous processes of the patient user to fixedly establish the spaced distance between the adjacent spinous processes. The clamp device 3102 may be inserted in either an assembled or disassembled configuration as dictated by specific needs and geometry of the patient user. A single incision may be made adjacent one medial-lateral side of the adjacent spinous processes, multiple incisions may be made adjacent both medial-lateral sides of the adjacent spinous processes, or a single incision in the medial-lateral center of the vertebrae may be made, to provide access for insertion of the clamp device 3102. The clamp may be assembled in whole or in part either before or after insertion into the patient user.

The clamp may be assembled as described above with the interior portions 3208 of both plates 3104, 3106 contacting each other, the nut 3902 tightly securing the arm 3126 and rod 3204, and set screws 3122, 3124 securingly engaged with the ridges 3202 to lock the longitudinal length of both plates 3104, 3106 to create a small minimized geometric insertion cross section for the assembly. The plates 3104, 3106 longitudinal length may be locked at the shortest length to minimize insertion geometry, or alternatively may be locked at a pre-established desirable length to fix the adjacent spinous processes.

After inserting the assembled clamp device 3102 in the patient user adjacent the spinous processes, the nut 3902 may be loosened to allow spaced distance between the plates 3104, 3106 and orient the plates on opposing medial-lateral surfaces of the spinous processes. The rotation capability between the plates 3104, 3106 assists in orienting the plates into proper configuration to abut the opposing surfaces of the spinous processes.

The rotation, or twist, capability between the two parts of each plate 3104, 3106 provides for abutment to the complex geometry of the adjacent spinous processes. The bony matter contacting surfaces 3310, 3416, 3510, 3618 may be externally forced adjacent the spinous processes, or alternatively, may be allowed to settle into a natural fit position adjacent the spinous processes. The twist capability between the parts and the rotation and translation adjustment between the plates provides for a secure abutment and fixation of the adjacent spinous processes by clamping device 3102.

Accordingly, the length of the plates 3104, 3106 may be established, if not established prior to insertion, by looseningly rotating the set screws 3122, 3124 and extending the plates from the shortest lengthwise configuration to the required length. The length is lockingly established by tighteningly rotating the set screws 3122, 3124 to engage ridges 3202. The length of plates 3104, 3106 may be established either before or after the inserted plates are configured on opposing surfaces of the spinous processes, however, greater ease of orientation and abutment of clamp device 3102 exists when the plates are configured in a reduced geometric size corresponding to the shortest length of the plates 3104, 3106.

Figure 40:
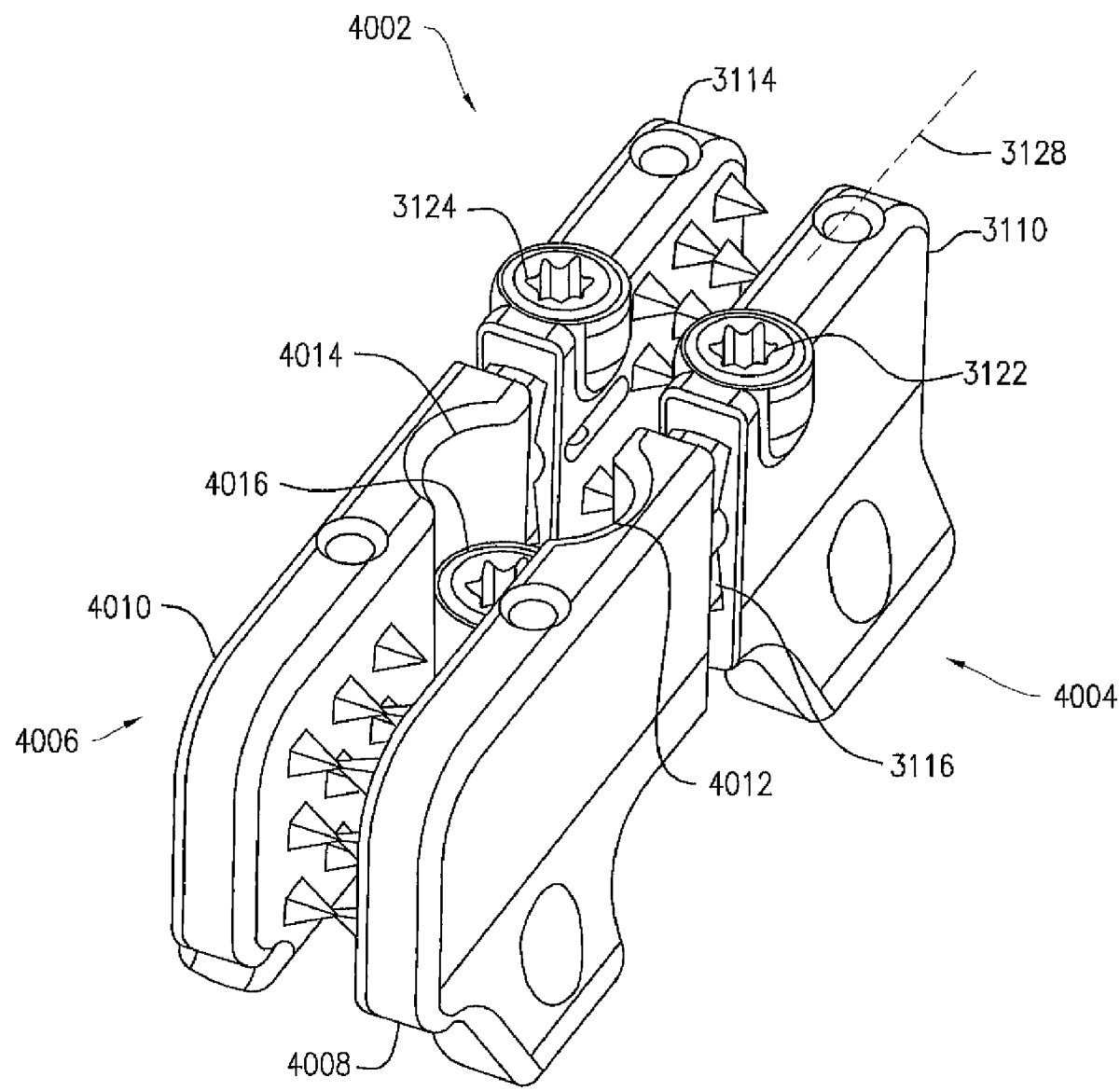
FIG. 40 illustrates a perspective view of a spinous process clamp according to another embodiment for mating to at least a portion of a spinous process.

FIG. 40 illustrates yet another exemplary spinous process clamp device 4002, for fixedly coupling adjacent spinous processes, according to some embodiments of the present invention. The clamp device 4002 is configured to incorporate some of the features of the devices described above with regard to FIGS. 1-39. In particular, like named elements include the same or similar characteristics as described above for the embodiment of clamp device 3102. Details with respect to common elements are referred to the description of clamp device 3102. New elements of the spinous process clamp device 4002 are described below.

In some embodiments, referring to FIG. 40, the spinous process clamp 4002 includes a first plate 4004 and a second plate 4006 angularly, rotationally, and translatingly coupled together and configured to abut the opposing bony matter surfaces of adjacent spinous processes.

Figure 41:
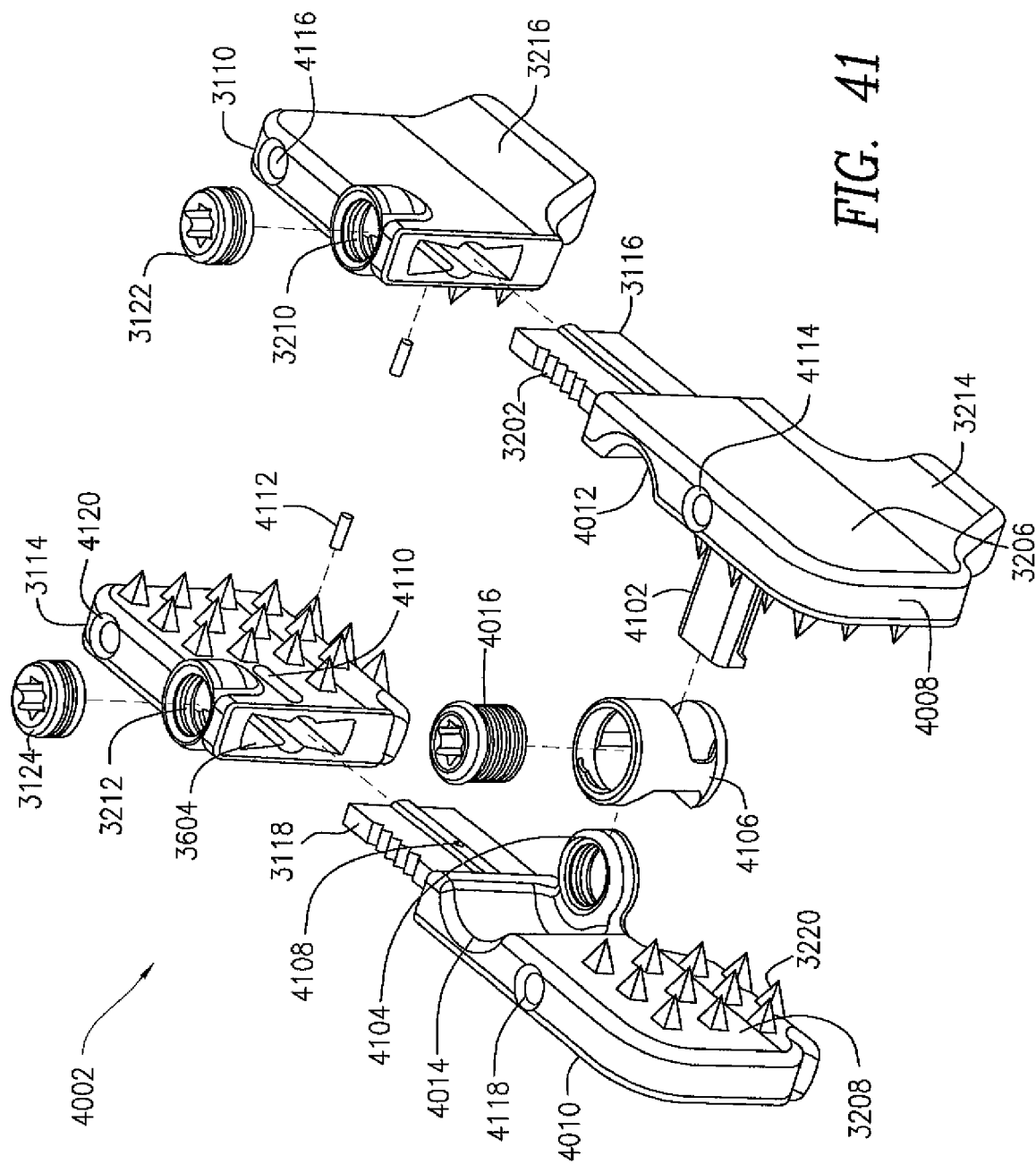
FIG. 41 is an exploded view of the spinous process clamp of FIG. 40 for mating to at least a portion of a spinous process.
Figure 42A:
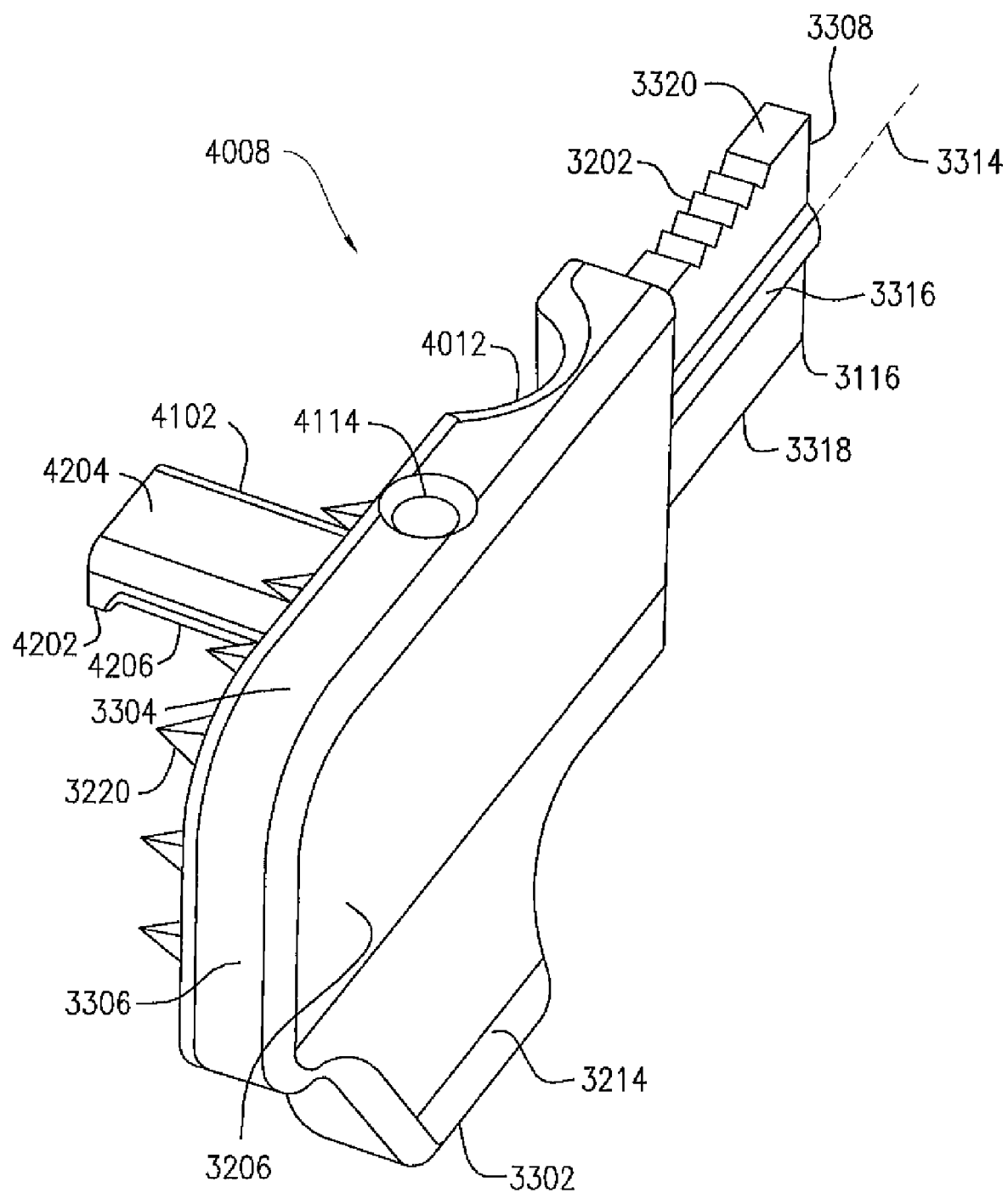
FIGS. 42a-42b illustrate perspective views of a first sliding part, or member, of the spinous process clamp of FIG. 40.
Figure 42B:
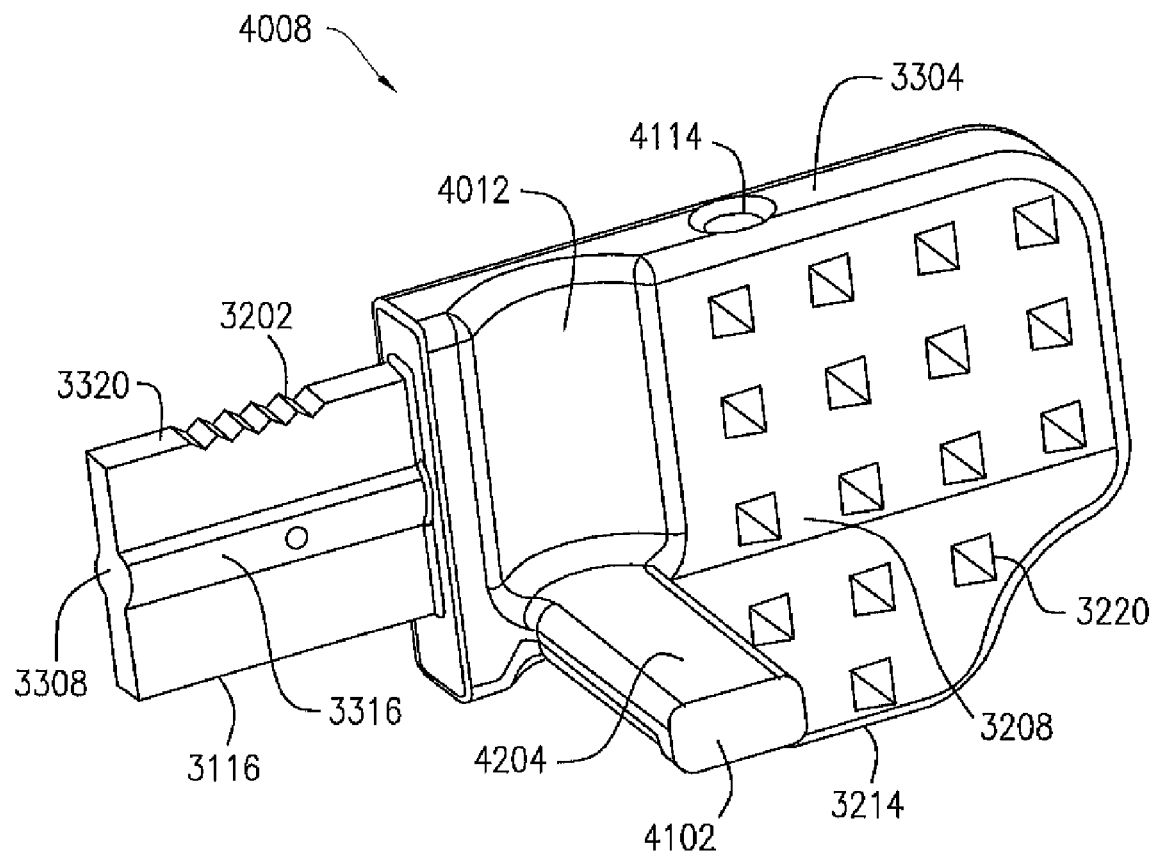

In some embodiments, referring to FIGS. 41 and 42a-42b, first plate 4004 includes a first sliding part 4008. First sliding part 4008 may be rotationally and translationally coupled to the second sliding part 3110 as described above with respect to device 3102 and generally has the same characteristics as first sliding part 3108 except for the differences associated with the coupling mechanism between the first plate 4004 and the second plate 4006 described further below.

First sliding part 4008 further includes a first recess 4012, a first arm 4102, and a second hole 4114. First recess 4012 is located on interior portion 3208, generally adjacent to the first extended portion 3116 of first sliding part 4008. First recess 4012 establishes a surface below interior portion 3208 in the direction of an exterior portion 3206. The first recess 4012 generally extends in an elongate direction normal to the longitudinal axis 3128 of the clamp device 4002. The first recess 4012 may extend from the first posterior face 3304 in the elongate direction through to the first anterior face 3302 of first sliding part 4008, spanning the full anterior-posterior width of first sliding part 4008. Alternatively the first recess 4012 may extend up to the first arm 4102. First recess 4012 as illustrated may have a geometric shape of a cylinder, however other geometric shapes are possible, e.g. a polygon, a triangle, an oval, or the like.

First arm 4102 extends away from the interior portion 3208 of first sliding part 4008 in a direction substantially normal to the generally flat surface of interior portion 3208 toward the second plate 4006. The cross section of the first arm 4102 may have a rectangular shape, although other geometric shapes are possible. The elongate direction of the rectangular cross section is parallel to the longitudinal axis of the clamp 4002. First arm 4102 includes a top face 4204, a bottom face 4206, and a lip 4202. Top face 4204 is generally flat and may be parallel to the longitudinal axis 3128 of clamp device 4002 and also is parallel to the first posterior face 3304. Bottom face 4206 is substantially parallel to top face 4204. The lip 4202 is a portion of the arm 4102 located on the bottom face 4206 adjacent the end farthest most away from the interior portion 3208 that protrudes in an anterior direction away from the bottom face 4204. First arm 4102 is configured to be received by a coupler 4016 described further below.

Second hole 4114 is located on the first posterior face 3304. Second hole 4114 establishes a coupling location for use in conjunction with instruments, and advantageously provides direct access for instruments from the posterior direction to the clamp device 4002. Clamp 4002 may include three additional and similar holes for use in conjunction with instruments, a third hole 4116, a fourth hole 4118, and a fifth hole 4120 as described below.

Figure 43:
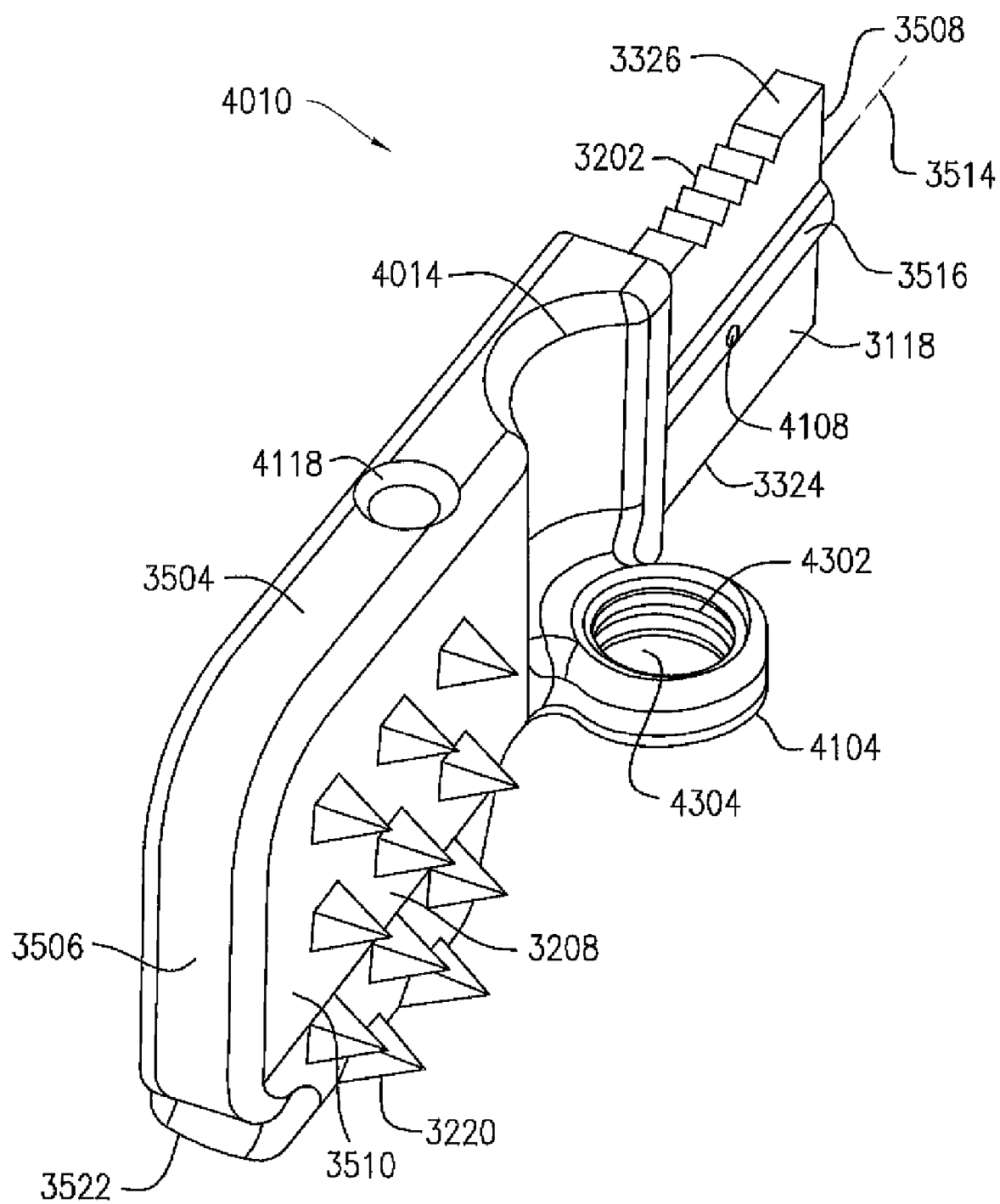
FIG. 43 illustrates a perspective view of a third sliding part, or member, of the spinous process clamp of FIG. 40.

In some embodiments, referring to FIGS. 41 and 43, second plate 4006 includes a third sliding part 4010 and a fourth sliding part 3114. Third sliding part 4010 may be rotationally and translationally coupled to the fourth sliding part 3114 as described above with respect to device 3102 and generally has the same characteristics as third sliding part 3112 except for the differences associated with the coupling mechanism between the first plate 4004 and the second plate 4006 described further below.

Third sliding part 4010 further includes a second recess 4014, a second arm 4104, and the fourth hole 4118. Second recess 4014 is located on interior portion 3208, generally adjacent to the second extended portion 3118 of third sliding part 4010. Second recess 4014 establishes a surface below interior portion 3208 in the direction of an exterior portion 3206. The second recess 4014 generally extends in an elongate direction normal to the longitudinal axis 3128 of the clamp device 4002. The second recess 4014 may extend from the third posterior face 3504 in the elongate direction through to the third anterior face 3502 of third sliding part 4010, spanning the full width of third sliding part 4010. Alternatively the second recess 4014 may extend up to the second arm 4104. Second recess 4014 as illustrated may have a geometric shape of a cylinder, however other geometric shapes are possible, e.g., a polygon, a triangle, an oval, or the like. Fourth hole 4118 is located on the third posterior face 3504 and is used in conjunction with instruments.

Second arm 4104 extends away from the interior portion 3208 of third sliding part 4010 in a direction substantially normal to the generally flat surface of interior portion 3208 toward the first plate 4004. The cross section of the second arm 4104 may have a circular shape, although other geometric shapes are possible. Second arm 4104 further includes threads 4302 and a sixth hole 4304. Sixth hole 4304 is adjacent the farthest most end of second arm 4104 away from interior portion 3208. Sixth hole 4304 extends through the second arm 4104 from the anterior face to the posterior face of the arm. The sixth hole 4304 is configured to receive a third securing screw 4016 described further below, thus generally has a circular shape. The threads 4302 are located on the inner diameter of the generally circular shape of sixth hole 4304. The threads are configured to couple to the third securing screw 4016, described below with respect to FIG. 45.

In some embodiments, referring again to FIG. 41, the device 4002 further includes a first hole 4108, a slot 4110, and a pin 4112. The first hole 4108 is located on the bony matter abutting side of the second extended portion 3118, more particularly on the third pivot surface 3516. The first hole 4108 is configured to receive the pin 4112. The slot 4110 is located on the interior portion 3208 of fourth sliding part 3114 and extends in an elongate direction parallel to the longitudinal axis of clamp 4002. The slot 4110 is located parallel and opposite the fourth pivot surface 3616 such that the slot 4110 will align with the first hole 4108 upon assembly of the second plate 4006. The pin 4112 is inserted, after assembly of second plate 4006, through the slot 4110 and securedly received into the first hole 4108. The pin 4112 establishes the sliding translation range of the second extended portion 3118 within second hollow interior 3604 as the pin 4112 contacts either end of the slot 4110 to establish translation maximums. Additionally, the same hole, pin, and slot configuration may be included on the first plate 4004 (not shown/labeled). Even further, the same hole, pin, and slot configuration may be included on the first plate 3104 and the second plate 3106 of the spinous process clamp device 3102 (not shown/labeled) described above.

The clamp 4002 may include four holes used in conjunction with insertion instruments having the already described second hole 4114 and the fourth hole 4118, as well as third hole 4116 located on the second posterior face 3406 of second sliding part 3110, and a fifth hole 4120 located on the fourth posterior face 3608 of the fourth sliding part 3114. The described instrument holes may additionally be included in an embodiment of the spinous process clamp 3102.

Figure 44:
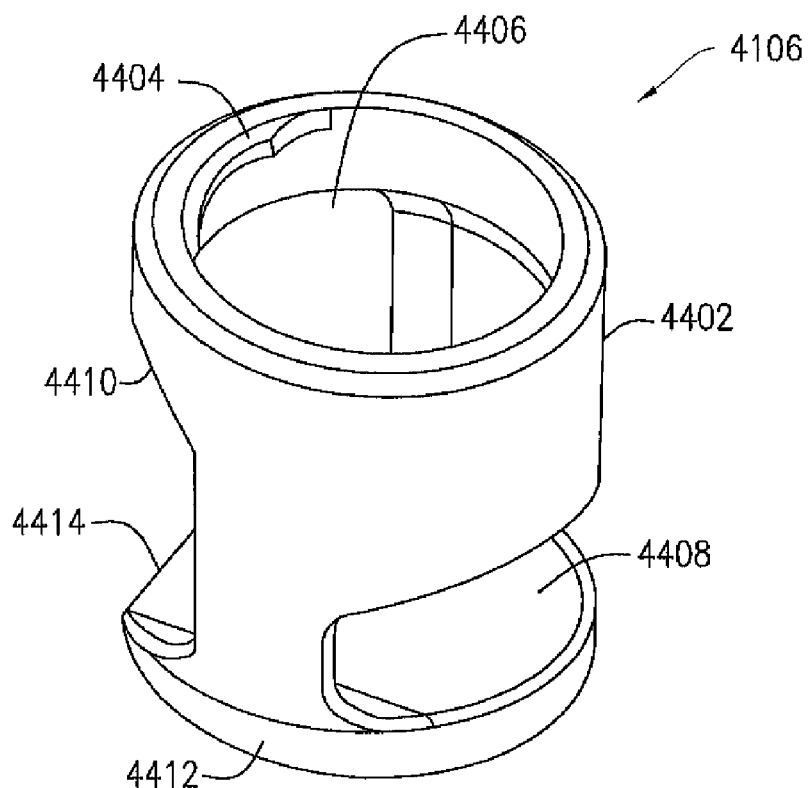
FIG. 44 illustrates a perspective view of a coupler configured to couple members of the spinous process clamp of FIG. 40.

FIG. 44 illustrates the coupler 4106. The coupler 4106 includes a body 4402, a coupler thread 4404, a first coupler opening 4406, a second coupler opening 4408, a third coupler opening 4410, and a base 4412. The body 4402 establishes the peripheral shape of the coupler 4106. The body 4402 generally is of cylindrical shape and is configured to receive the third securing screw 4016, as well as the first arm 4102 and the second arm 4104 described further below. The first coupler opening 4406 is located on the farthest posterior end of the coupler 4106, creating an open end of the cylinder shaped body 4402. The first coupler opening 4406 is configured to receive the third securing screw 4016. The coupler thread 4404 may be similar to the typical internal fastener thread, and includes at least a portion of one lead. The coupler thread 4404 is located on the inner diameter established by the body 4402 and is adjacent the farthest posterior end of the coupler 4106 and adjacent the second coupler opening 4408.

The second coupler opening 4408 is located on the portion of the coupler 4106 that is nearest to the first plate 4004 and adjacent the farthest anterior end of the coupler 4106, establishing an opening in the cylindrical periphery of the coupler 4106. The third coupler opening 4410 is located on the portion of the coupler 4106 that is nearest to the second plate 4006 and adjacent the farthest anterior end of the coupler 4106, establishing an opening in the cylindrical periphery of the coupler 4106. As illustrated, the third coupler opening 4410 is larger than the second coupler opening 4408, however the second coupler opening 4408 may be smaller, larger, or the same size as the third coupler opening 4410 as desired. The third coupler opening 4410 is substantially parallel to the second coupler opening 4408 such that the two openings are on opposite sides of the coupler 4106.

The base 4412 establishes the end of the coupler 4106 that opposes the first coupler opening 4406, thus is located on the farthest anterior end of the coupler 4106. As illustrated, the base 4412 establishes a closed end of the cylinder, however other configurations are possible, e.g. slotted, holes, open, or the like. The base 4412 may have a straight side or edge such that the base 4412 does not establish a full circle. The straight side or edge is substantially parallel to the third opening 4410 and is located on the portion of the coupler 4106 that is nearest to the second plate 4006.

Figure 45:
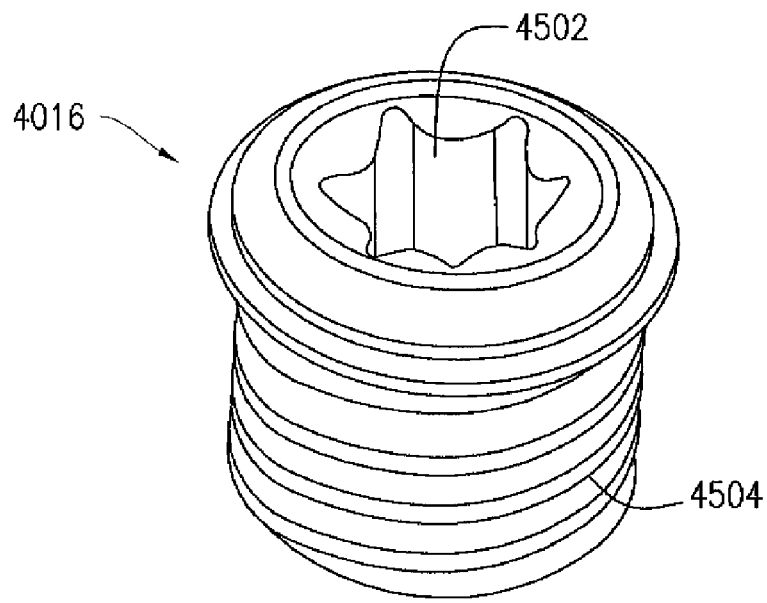
FIG. 45 illustrates a perspective view of a securing screw configured to couple members of the spinous process clamp of FIG. 40.

FIG. 45 illustrates the third securing screw 4016. In some embodiments, the third securing screw 4016 can include a threaded cylinder, or a functional equivalent, that establishes the desired distance, or gap, as well as the angled relationship between the first plate 4004 and the second plate 4006 by locking the coupled relationship between the first sliding part 4008 and the third sliding part 4010. The third securing screw 4016 has a recess 4502 configured to accommodate wrenches as described for screws 110 and 3122 above, to allow installation into the first coupler opening 4406 by rotatingly engaging the threads 4504 of the screw with the coupler thread 4404 in the first coupler opening 4406. Alternatively, other fastening mechanisms known in the art may be used to secure the two angularly and translationally coupled plates 4004, 4006.

The spinous process clamping device 4002 is coupled together via the coupler 4106, the third securing screw 4016, the first arm 4102, and the second arm 4104. The coupler 4106 is configured to receive the other three elements. The first arm 4102 is received by the coupler 4106 through the second coupler opening 4408 and is generally located adjacent and parallel to the base 4412 such that the bottom face 4206 contacts the inner coupler 4106 surface of the base 4412. The first arm 4102 is coupled to the coupler 4106 such that the lip 4202 of the first arm 4102 is located at least beyond the straight edge of base 4412. The lip 4202 mitigates the likelihood of the arm unexpectedly backing out of the coupler 4106 by creating a physical stop that will butt up against the straight edge 4414 and prevent further movement in the exiting, or backing out, direction.

The second arm 4104 is received by the coupler 4106 through the third coupler opening 4410 and is generally located posterior to the first arm 4102. This arrangement establishes contact between the anterior side of the second arm 4104 and the top face 4204 of the first arm 4102. The second arm 4104 is inserted to the coupler a distance sufficient to align the center of the sixth hole 4304 of the second arm 4104 and the center of the first coupler opening 4406 of the coupler 4106. The third securing screw 4016 is received by first the coupler 4106 elements of the thread 4404 and by the first coupler opening 4406. The third securing screw 4016 is next received by internal threads 4302 of the hole 4304 of the second arm 4104. The third securing screw 4016 is received by rotatingly engaging the external threads 4504 with the corresponding thread 4404 and threads 4302.

The spaced and angular relationship between the first plate 4004 and the second plate 4006, or the first sliding part 4008 and the third sliding part 4010, are established by securingly rotating the third set screw 4016 until tight. The anterior end of the third set screw 4016 will rotatingly engage coupler 4106 and the second arm 4104, bringing the second arm 4104 toward first coupler opening 4406 and then extend through the anterior end of sixth hole 4304 to contact the first arm 4102 and snugly push the first arm 4102 against the base 4412. Sufficient force in rotation of third set screw 4016 will lock the translation of first arm 4102 through coupler 4106, which establishes the spaced distance, or gap, between the first plate 4004 and the second plate 4006. Sufficient rotation force will also lock the angular rotation, or relationship between the first plate 4004 and the second plate 4006, about the substantially common center of the third set screw 4016 and the coupler 4106 first opening 4406 and the sixth hole 4304 of the second arm 4104.

Rotation of the two plates about the substantially common center prior to tight rotation of the third set screw 4016 advantageously allows the clamp 4002 to vary the angular relationship of the two plates upon insertion to the patient user and conform to the complex geometry of the adjacent spinous processes. The magnitude of angular rotation between the first plate 4004 and the second plate 4006 is determined by the relative difference between the circumferential width of the second coupler opening 4408 and the longitudinal width of the first arm 4102, as well as the relative difference between the circumferential width of the third coupler opening 4410 and the longitudinal width of the second arm 4104. The magnitude of the translation of first arm 4102 through the coupler 4106 is determined by the depth of the second recess 4014 and the longitudinal width of the first arm 4102.

Upon insertion into a patient user, the overall cross-sectional footprint of the assembled clamp, if assembled prior to insertion, may be minimized by the first arm 4102 fully engaging the coupler 4106 by maximum translation and allowing the end of the second arm 4104 to be received into the first recess 4012 such that the opposing bony matter contacting surfaces of the first plate 4004 and the second plate 4006 are as close together as possible.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described example embodiments, but should be defined only in accordance with the following claims and their equivalents.

What is claimed is:

1. A spinous process device, comprising:
   a first plate extending along a first pivot axis comprising:
      a first part configured to abut a first spinous process having an extended portion;
      a second part configured to abut a second spinous process having a hollow interior portion,
      wherein the extended portion of the first part is slidably received into the hollow interior portion of the second part along the first pivot axis;
   a second plate extending along a second pivot axis comprising:
      a third part configured to abut the first spinous process opposite the first part having an extended portion; and
      a fourth part configured to abut the second spinous process opposite the second part having a hollow interior portion,
      wherein the extended portion of the third part is slidably received into the hollow interior portion of the fourth part along the second pivot axis; and
   a coupling mechanism configured to couple the first and second plates such that:
      the distance between the first plate and the second plate is adjustable; and
      the first part and the third part are rotatable relative to each other.

2. The device according to claim 1, wherein the first part comprises a first member extending toward the third part, and the third part comprises a second member extending toward the first part, wherein the first member is coupled to the second member with the coupling mechanism that allows the first member to translate axially and rotate relative to the second member to establish a spaced distance between the first part and the third part and to establish an angular relationship between the first part and the third part.

3. The device according to claim 2, wherein the coupling mechanism comprises a clevis, the clevis comprising an aperture, a body and a threaded end, wherein the first member is a rod and the second member is an arm, the rod being coupled to the arm with the rod extending through the aperture and translating axially through the aperture to establish a spaced distance between the first part and the third part, and the arm rotates about the clevis body to establish an angular relationship between the first part and the third part.

4. The device according to claim 2, wherein the coupling mechanism comprises a hollow cylinder having a first opening, a second opening, and a third opening, the first member is a first arm and the second member is a second arm comprising a threaded hole, wherein the first plate is coupled to the second plate with the first arm received in the second opening of the hollow cylinder, the second arm received in the third opening of the hollow cylinder, and wherein a securing screw extends into the first opening of the hollow cylinder and engages the threaded hole in the second arm.

5. The device according to claim 1, wherein at least one of the first part, second part, third part and fourth part includes an interior surface with a plurality of protrusions configured to interact with the spinous processes.

6. The device according to claim 1, wherein each of the first part, second part, third part and fourth part includes an instrument coupling hole.

7. The device according to claim 1, wherein the second part is rotatable relative to the first part along the first pivot axis and the fourth part is rotatable relative to the third part along the second pivot axis.

8. A method of clamping adjacent spinous processes of a patient, comprising:
providing a spinous process clamping device comprising:
a first part and a second part slidingly coupled to form a first plate, wherein the first part comprises an extended portion receivable into a hollow interior portion of the second part;
a third part and a fourth part slidingly coupled to form a second plate, wherein the third part comprises an extended portion receivable into a hollow interior portion of the fourth part;
a coupling mechanism configured to couple the first and second plates to allow for adjustment of distance and relative rotation between the first and second plates;
inserting the spinous process clamping device adjacent at least two adjacent spinous process with the first plate provided on one side of the two adjacent spinous processes and the second plate provided on the other side of the two adjacent spinous process;
clamping the first plate and second plates to the opposite sides of the two adjacent spinous processes, wherein said clamping comprises:
adjusting lengths of the first plate and the second plate by sliding the extended portion of the first part relative to the hollow interior portion of the second part and sliding the extended portion of the third part relative to the hollow interior portion of the fourth part, respectively, to a desired length for placement of the first and second plates against the two adjacent spinous processes;
adjusting an angular relationship of the first plate relative to the second plate via the coupling mechanism connecting the first plate to the second plate, to conform to the shape of the adjacent spinous processes.

9. The method according to claim 8, wherein after adjusting lengths of the first plate and the second plate, the clamping the first plate and second plates further comprises adjusting an angular relationship of the first and second parts of the first plate by twisting the first part relative to the second part, and adjusting the angular relationship of the third and fourth parts of the second plate by twisting the third part relative to the fourth part, to conform to the shape of the adjacent spinous processes.

10. A spinous process device, comprising:
a first plate extending along a first pivot axis comprising:
a first part configured to abut a first spinous process;
a second part configured to abut a second spinous process,
wherein the first part is slidably coupled to the second part along the first pivot axis and the second part is rotatable relative to the first part;
a second plate extending along a second pivot axis comprising:
a third part configured to abut the first spinous process opposite the first part; and
a fourth part configured to abut the second spinous process opposite the second part,
wherein the third part is slidably coupled to the fourth part along the second pivot axis and the fourth part is rotatable relative to the third part; and
a coupling mechanism configured to couple the first and second plates such that:
the distance between the first plate and the second plate is adjustable; and
the first part and the third part are rotatable relative to each other;
wherein the first part comprises a first member extending toward the third part, and the third part comprises a second member extending toward the first part, wherein the first member is coupled to the second member with the coupling mechanism that allows the first member to translate axially and rotate relative to the second member to establish a spaced distance between the first part and the third part and to establish an angular relationship between the first part and the third part;
wherein the coupling mechanism comprises a clevis, the clevis comprising an aperture, a body and a threaded end, wherein the first member is a rod and the second member is an arm, the rod being coupled to the arm with the rod extending through the aperture and translating axially through the aperture to establish a spaced distance between the first part and the third part, and the arm rotates about the clevis body to establish an angular relationship between the first part and the third part.

11. The device according to claim 10, wherein at least one of the first part, second part, third part and fourth part includes an interior surface with a plurality of protrusions configured to interact with the spinous processes.

12. The device according to claim 10, wherein each of the first part, second part, third part and fourth part includes an instrument coupling hole.

13. A spinous process device, comprising:
a first plate extending along a first pivot axis comprising:
a first part configured to abut a first spinous process;
a second part configured to abut a second spinous process,
wherein the first part is slidably coupled to the second part along the first pivot axis and the second part is rotatable relative to the first part;
a second plate extending along a second pivot axis comprising:
a third part configured to abut the first spinous process opposite the first part; and
a fourth part configured to abut the second spinous process opposite the second part,
wherein the third part is slidably coupled to the fourth part along the second pivot axis and the fourth part is rotatable relative to the third part; and
a coupling mechanism configured to couple the first and second plates such that:

the distance between the first plate and the second plate is adjustable; and the first part and the third part are rotatable relative to each other;

wherein the first part comprises a first member extending toward the third part, and the third part comprises a second member extending toward the first part, wherein the first member is coupled to the second member with the coupling mechanism that allows the first member to translate axially and rotate relative to the second member to establish a spaced distance between the first part and the third part and to establish an angular relationship between the first part and the third part;

wherein the coupling mechanism comprises a hollow cylinder having a first opening, a second opening, and a third opening, the first member is a first arm and the second member is a second arm comprising a threaded hole, wherein the first plate is coupled to the second plate with the first arm received in the second opening of the hollow cylinder, the second arm received in the third opening of the hollow cylinder, and wherein a securing screw extends into the first opening of the hollow cylinder and engages the threaded hole in the second arm.

14. The device according to claim 13, wherein at least one of the first part, second part, third part and fourth part includes an interior surface with a plurality of protrusions configured to interact with the spinous processes.

15. The device according to claim 13, wherein each of the first part, second part, third part and fourth part includes an instrument coupling hole.

* * * * *